US009999657B2

(12) United States Patent
Bossard et al.

(10) Patent No.: US 9,999,657 B2
(45) Date of Patent: *Jun. 19, 2018

(54) POLYMER-FACTOR VIII MOIETY CONJUGATES

(71) Applicant: Nektar Therapeutics, San Francisco, CA (US)

(72) Inventors: Mary J. Bossard, Madison, AL (US); Michael D. Bentley, Huntsville, AL (US); Ping Zhang, Madison, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/964,416

(22) Filed: Dec. 9, 2015

(65) Prior Publication Data

US 2016/0175402 A1 Jun. 23, 2016

Related U.S. Application Data

(63) Continuation of application No. 14/517,679, filed on Oct. 17, 2014, now abandoned, which is a continuation of application No. 13/431,844, filed on Mar. 27, 2012, now Pat. No. 8,889,831, which is a continuation of application No. 12/636,594, filed on Dec. 11, 2009, now Pat. No. 8,247,536, which is a continuation of application No. 11/702,302, filed on Feb. 5, 2007, now Pat. No. 7,858,749, which is a continuation of application No. 10/789,956, filed on Feb. 26, 2004, now Pat. No. 7,199,223.

(60) Provisional application No. 60/450,578, filed on Feb. 26, 2003.

(51) Int. Cl.
| C07K 14/755 | (2006.01) |
| A61K 38/37 | (2006.01) |
| A61K 47/10 | (2017.01) |
| A61K 47/60 | (2017.01) |

(52) U.S. Cl.
CPC .............. *A61K 38/37* (2013.01); *A61K 47/10* (2013.01); *A61K 47/60* (2017.08)

(58) Field of Classification Search
None
See application file for complete search history.

(56) References Cited

U.S. PATENT DOCUMENTS

| 4,179,337 A | 12/1979 | Davis et al. |
| 4,650,858 A | 3/1987 | Rasmussen et al. |
| 4,757,006 A | 7/1988 | Toole, Jr. et al. |
| 4,831,119 A | 5/1989 | Nordfang et al. |
| 4,868,122 A | 9/1989 | Kominek et al. |
| 4,970,300 A | 11/1990 | Fulton et al. |
| 4,994,439 A | 2/1991 | Longenecker et al. |
| 5,259,951 A | 11/1993 | Arrighi et al. |
| 5,298,643 A | 3/1994 | Greenwald |
| 5,397,771 A | 3/1995 | Bechgaard et al. |
| 5,565,427 A | 10/1996 | Freudenburg |
| 5,567,422 A | 10/1996 | Greenwald |
| 5,618,788 A | 4/1997 | Capon et al. |
| 5,618,789 A | 4/1997 | Capon et al. |
| 5,621,039 A | 4/1997 | Hallahan et al. |
| 5,637,749 A | 6/1997 | Greenwald |
| 5,739,208 A | 4/1998 | Harris |
| 5,766,897 A | 6/1998 | Braxton |
| 5,804,420 A | 9/1998 | Chan et al. |
| 5,932,462 A | 8/1999 | Harris et al. |
| 5,972,885 A | 10/1999 | Spira et al. |
| 6,037,452 A | 3/2000 | Minamino et al. |
| 6,048,720 A | 4/2000 | Dalborg et al. |
| 7,199,223 B2 | 4/2007 | Bossard et al. |
| 7,858,749 B2 | 12/2010 | Bossard et al. |
| 7,863,421 B2 | 1/2011 | Bossard et al. |
| 8,133,977 B2 | 3/2012 | Bossard et al. |
| 8,143,378 B2 | 3/2012 | Bossard et al. |
| 8,247,536 B2 | 8/2012 | Bossard et al. |
| 8,889,831 B2 | 11/2014 | Bossard et al. |
| 2003/0077752 A1 | 4/2003 | Cho et al. |
| 2003/0118510 A1 | 6/2003 | Patton et al. |
| 2003/0161791 A1 | 8/2003 | Bentley et al. |
| 2003/0166536 A1 | 9/2003 | Lollar |
| 2004/0116649 A1 | 6/2004 | Kozlowski |
| 2005/0014903 A1 | 1/2005 | Kozlowski et al. |
| 2008/0058504 A1 | 3/2008 | Bossard et al. |
| 2009/0041714 A1 | 2/2009 | Bossard et al. |
| 2012/0244597 A1 | 9/2012 | Bossard et al. |

(Continued)

FOREIGN PATENT DOCUMENTS

| EP | 0871649 | 10/1998 |
| EP | 1260582 A1 | 11/2002 |

(Continued)

OTHER PUBLICATIONS

Enzon Pharmaceuticals, "Macromolecular Engineering Technologies", pp. 1-14 (2004).
Greenwald et al., "Effective drug delivery by PEGylated drug conjugates", Adv. Drug Del. Rev., vol. 55, No. 2, pp. 217-250 (2003).
Japanese Office Action dated Mar. 18, 2010 from related JP Patent Application No. 2006-503916.
Harris et al., "Effect of pegylation on pharmaceuticals", Nat. Rev., vol. 2, No. 3, pp. 214-221 (2003).
Lind et al., "Novel forms of B-domain-deleted recombinant factor VIII molecules construction and biochemical characterization", Eur. J. Biochem., vol. 232, pp. 19-27 (1995).
Nektar Transforming Therapeutics, "Nektar molecule engineering: Polyethylen Glycol and derivatives for advanced PEGylation", pp. 10-20, Catalog (2003).

(Continued)

Primary Examiner — Hope Robinson
(74) Attorney, Agent, or Firm — Susan T. Evans

(57) ABSTRACT

Conjugates of a Factor VIII moiety and one or more water-soluble polymers are provided. Typically, the water-soluble polymer is poly(ethylene glycol) or a derivative thereof. Also provided are compositions comprising the conjugates, methods of making the conjugates, and methods of administering compositions comprising the conjugates to a patient.

22 Claims, 6 Drawing Sheets

(56) References Cited

U.S. PATENT DOCUMENTS

| | | |
|---|---|---|
| 2012/0245289 A1 | 9/2012 | Bossard et al. |
| 2015/0038422 A1* | 2/2015 | Bossard ........... A61K 47/48215 514/14.1 |

FOREIGN PATENT DOCUMENTS

| | | |
|---|---|---|
| JP | 59-172425 | 9/1984 |
| JP | 05-502161 | 4/1993 |
| JP | 11-513378 | 11/1999 |
| JP | 2001-526238 A | 12/2001 |
| WO | WO 1991/009122 | 6/1991 |
| WO | WO 1992/016555 | 10/1992 |
| WO | WO 1994/004193 | 3/1994 |
| WO | WO 1994/015625 | 7/1994 |
| WO | WO 1996/041813 A2 | 12/1996 |
| WO | WO 1997/011957 | 4/1997 |
| WO | WO 1998/051341 | 11/1998 |
| WO | WO 1999/005333 | 2/1999 |
| WO | WO 1999/032134 A1 | 7/1999 |
| WO | WO 2000/042175 A1 | 7/2000 |
| WO | WO 2000/078302 | 12/2000 |
| WO | WO 2001/062827 | 8/2001 |
| WO | WO 2001/087925 A1 | 11/2001 |
| WO | WO 2002/009766 | 2/2002 |
| WO | WO 2002/059179 | 8/2002 |
| WO | WO 2004/022629 | 3/2004 |
| WO | WO 2004/060406 | 7/2004 |
| WO | WO 2004/060967 A1 | 7/2004 |
| WO | WO 2004/063250 A1 | 7/2004 |
| WO | WO 2004/084948 | 10/2004 |
| WO | WO 2004/091499 | 10/2004 |
| WO | WO 2004/099231 | 11/2004 |
| WO | WO 2005/000360 | 1/2005 |

OTHER PUBLICATIONS

Nektar Transforming Therapeutics, "Nektar advanced PEGylation: Polyethylene glycol and derivatives for advanced PEGylation", pp. 1-24, Catalog (2004).
NOF Corporation, "PEG derivatives, phospholipid and drug delivery materials for pharmaceuticals", pp. 1-46, Catalog (2003)—1st.
NOF Corporation, "PEG derivatives, phospholipid and drug delivery materials for pharmaceuticals", pp. 1-50, Catalog (2003)—2nd.
NOF Corporation, "PEG derivatives, phospholipids and drug delivery materials for pharmaceutical products and formulations", pp. 1-59, Catalog Ver. 8 (2006).
Ouchi et al., "Design of antitumor agent-terminated poly(ethylene glycol) conjugate as macromolecular prodrug", Polymer Preprints, vol. 38, No. 1, pp. 582-583 (1997).
PCT International Search Report, PCT Application No. PCT/US2004/006034, dated Nov. 29, 2004.
Polypure, "Products; PEG amines; PEG acids and amino acids; PEG thiols and disulfides", Biotins, (2004).
Polypure, "Products; PEG amines; PEG acids and amino acids; PEG thiols and disulfides", Biotins (2005).
Quanta Biodesign, "Labeling, derivatization and crosslinking reagents for biological and related materials with dPEG", pp. 1-38, Mar. 12, 2004.
Quanta Biodesign, "Labeling, modification and crosslinking reagents incorporating our unique monodispersed dPEG technology", pp. 1-31, Nov. 5, 2004.
Quanta Biodesign, "Leading innovator, producer and provider of monodisperse discrete PEG (dPEG) derivatives", pp. 1-51, updated Jul. 18, 2005.
Quanta Biodesign, "Leading innovator, producer and provider of monodisperse discrete PEG (dPEG) derivatives", pp. 1-51, updated Nov. 17, 2005.
Rostin et al., "B-domain deleted recombinant coagulation factor VII modified with monomethoxypolyethelyne glycol", Bioconjugate Chem., vol. 11, pp. 387-396 (2000).
Shearwater Polymers, Inc., pp. 2-49, Catalog (1995).
Shearwater Polymers, Inc., "Polyethylene Glycol and derivatives", pp. 1-53, Catalog (1997).
Shearwater Polymers, Inc., "Polyethylene glycol and derivatives: Functionalized biocompatible polymers for research and pharmaceuticals", pp. 1-50, Catalog (2000).
Shearwater Corporation, "Polyethylene clycol and derivatives for biomedical applications", pp. 1-17, Catalog (2001).
Sims et al., "A Method for the estimation of polyethylene glycol in plasma protein fractions", Analytical Biochemistry, vol. 107, pp. 60-63, (1980).
Veronese et al., "Peptide and protein PEGylation: A review of problem and solutions", Biomaterials, vol. 22, pp. 405-417 (2001).
Zalipsky, "Chemistry of polyethylene glycol conjugates with biologically active molecules", Adv. Drug Delivery Reviews, vol. 16, pp. 157-182 (1995).
Zalipsky et al., "Use of functionalized poly(ethylene glycol)s for modification of polypeptides in polyethylene glycol chemistry: Biotechnical and biomedical applications", Plenum Press, N.Y., pp. 347-370 (1992).
In the United States District Court for the Northern District of California , Case 3:17-cv-05055: in Re.: *Bayer Healthcare LLC* v. *Nektar Therapeutics, Baxalta Incorporated and Baxalta US INC.*: Complaint for Declaratory Judgement of Patent Non-Infringement and Invalidity, 24 pages. Aug. 2017.

* cited by examiner

SEQUENCE LISTING

```
<160> NUMBER OF SEQ ID NOS: 2

<210> SEQ ID NO 1
<211> LENGTH: 2351
<212> TYPE: PRT
<213> ORGANISM: Homo sapiens

<400> SEQUENCE: 1

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
            85                  90                  95

Ala Glu Val Tyr Asp Thr Val Val Ile Thr Leu Lys Asn Met Ala Ser
        100                 105                 110

His Pro Val Ser Leu His Ala Val Gly Val Ser Tyr Trp Lys Ala Ser
    115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
            165                 170                 175

Tyr Leu Ser His Val Asp Leu Val Lys Asp Leu Asn Ser Gly Leu Ile
        180                 185                 190

Gly Ala Leu Leu Val Cys Arg Glu Gly Ser Leu Ala Lys Glu Lys Thr
    195                 200                 205

Gln Thr Leu His Lys Phe Ile Leu Leu Phe Ala Val Phe Asp Glu Gly
```

```
              210                 215                 220
Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
                260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
        290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
        370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Val Arg Phe Met
            435                 440                 445

Ala Tyr Thr Asp Glu Thr Phe Lys Thr Arg Glu Ala Ile Gln His Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640
```

```
Phe Asp Ser Leu Gln Leu Ser Val Cys Leu His Glu Val Ala Tyr Trp
            645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
            675                 680                 685
Leu Phe Pro Phe Ser Gly Glu Thr Val Phe Met Ser Met Glu Asn Pro
            690                 695                 700
Gly Leu Trp Ile Leu Gly Cys His Asn Ser Asp Phe Arg Asn Arg Gly
705                 710                 715                 720
Met Thr Ala Leu Leu Lys Val Ser Cys Asp Lys Asn Thr Gly Asp
            725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Ser Arg His Pro
            755                 760                 765
Ser Thr Arg Gln Lys Gln Phe Asn Ala Thr Thr Ile Pro Glu Asn Asp
            770                 775                 780
Ile Glu Lys Thr Asp Pro Trp Phe Ala His Arg Thr Pro Met Pro Lys
785                 790                 795                 800
Ile Gln Asn Val Ser Ser Ser Asp Leu Leu Met Leu Leu Arg Gln Ser
            805                 810                 815
Pro Thr Pro His Gly Leu Ser Leu Ser Asp Leu Gln Glu Ala Lys Tyr
            820                 825                 830
Glu Thr Phe Ser Asp Asp Pro Ser Pro Gly Ala Ile Asp Ser Asn Asn
            835                 840                 845
Ser Leu Ser Glu Met Thr His Phe Arg Pro Gln Leu His His Ser Gly
            850                 855                 860
Asp Met Val Phe Thr Pro Glu Ser Gly Leu Gln Leu Arg Leu Asn Glu
865                 870                 875                 880
Lys Leu Gly Thr Thr Ala Ala Thr Glu Leu Lys Lys Leu Asp Phe Lys
            885                 890                 895
Val Ser Ser Thr Ser Asn Asn Leu Ile Ser Thr Ile Pro Ser Asp Asn
            900                 905                 910
Leu Ala Ala Gly Thr Asp Asn Thr Ser Ser Leu Gly Pro Pro Ser Met
            915                 920                 925
Pro Val His Tyr Asp Ser Gln Leu Asp Thr Thr Leu Phe Gly Lys Lys
            930                 935                 940
Ser Ser Pro Leu Thr Glu Ser Gly Gly Pro Leu Ser Leu Ser Glu Glu
945                 950                 955                 960
Asn Asn Asp Ser Lys Leu Leu Glu Ser Gly Leu Met Asn Ser Gln Glu
            965                 970                 975
Ser Ser Trp Gly Lys Asn Val Ser Ser Thr Glu Ser Gly Arg Leu Phe
            980                 985                 990
Lys Gly Lys Arg Ala His Gly Pro Ala Leu Leu Thr Lys Asp Asn Ala
            995                 1000                1005
Leu Phe Lys Val Ser Ile Ser Leu Leu Lys Thr Asn Lys Thr Ser
            1010                1015                1020
Asn Asn Ser Ala Thr Asn Arg Lys Thr His Ile Asp Gly Pro Ser
            1025                1030                1035
Leu Leu Ile Glu Asn Ser Pro Ser Val Trp Gln Asn Ile Leu Glu
            1040                1045                1050
```

```
Ser Asp Thr Glu Phe Lys Lys Val Thr Pro Leu Ile His Asp Arg
1055                1060                1065

Met Leu Met Asp Lys Asn Ala Thr Ala Leu Arg Leu Asn His Met
1070                1075                1080

Ser Asn Lys Thr Thr Ser Ser Lys Asn Met Glu Met Val Gln Gln
1085                1090                1095

Lys Lys Glu Gly Pro Ile Pro Pro Asp Ala Gln Asn Pro Asp Met
1100                1105                1110

Ser Phe Phe Lys Met Leu Phe Leu Pro Glu Ser Ala Arg Trp Ile
1115                1120                1125

Gln Arg Thr His Gly Lys Asn Ser Leu Asn Ser Gly Gln Gly Pro
1130                1135                1140

Ser Pro Lys Gln Leu Val Ser Leu Gly Pro Glu Lys Ser Val Glu
1145                1150                1155

Gly Gln Asn Phe Leu Ser Glu Lys Asn Lys Val Val Val Gly Lys
1160                1165                1170

Gly Glu Phe Thr Lys Asp Val Gly Leu Lys Glu Met Val Phe Pro
1175                1180                1185

Ser Ser Arg Asn Leu Phe Leu Thr Asn Leu Asp Asn Leu His Glu
1190                1195                1200

Asn Asn Thr His Asn Gln Glu Lys Lys Ile Gln Glu Glu Ile Glu
1205                1210                1215

Lys Lys Glu Thr Leu Ile Gln Glu Asn Val Val Leu Pro Gln Ile
1220                1225                1230

His Thr Val Thr Gly Thr Lys Asn Phe Met Lys Asn Leu Phe Leu
1235                1240                1245

Leu Ser Thr Arg Gln Asn Val Glu Gly Ser Tyr Asp Gly Ala Tyr
1250                1255                1260

Ala Pro Val Leu Gln Asp Phe Arg Ser Leu Asn Asp Ser Thr Asn
1265                1270                1275

Arg Thr Lys Lys His Thr Ala His Phe Ser Lys Lys Gly Glu Glu
1280                1285                1290

Glu Asn Leu Glu Gly Leu Gly Asn Gln Thr Lys Gln Ile Val Glu
1295                1300                1305

Lys Tyr Ala Cys Thr Thr Arg Ile Ser Pro Asn Thr Ser Gln Gln
1310                1315                1320

Asn Phe Val Thr Gln Arg Ser Lys Arg Ala Leu Lys Gln Phe Arg
1325                1330                1335

Leu Pro Leu Glu Glu Thr Glu Leu Glu Lys Arg Ile Ile Val Asp
1340                1345                1350

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser His Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser His Leu Pro Ala Ala Ser Tyr Arg Lys Lys
1430                1435                1440

Asp Ser Gly Val Gln Glu Ser Ser His Phe Leu Gln Gly Ala Lys
```

-continued

```
            1445                1450                1455
Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845
```

-continued

Phe Asp Cys Lys Ala Trp Ala Tyr Phe Ser Asp Val Asp Leu Glu
    1850            1855                1860

Lys Asp Val His Ser Gly Leu Ile Gly Pro Leu Leu Val Cys His
    1865            1870                1875

Thr Asn Thr Leu Asn Pro Ala His Gly Arg Gln Val Thr Val Gln
    1880            1885                1890

Glu Phe Ala Leu Phe Phe Thr Ile Phe Asp Glu Thr Lys Ser Trp
    1895            1900                1905

Tyr Phe Thr Glu Asn Met Glu Arg Asn Cys Arg Ala Pro Cys Asn
    1910            1915                1920

Ile Gln Met Glu Asp Pro Thr Phe Lys Glu Asn Tyr Arg Phe His
    1925            1930                1935

Ala Ile Asn Gly Tyr Ile Met Asp Thr Leu Pro Gly Leu Val Met
    1940            1945                1950

Ala Gln Asp Gln Arg Ile Arg Trp Tyr Leu Leu Ser Met Gly Ser
    1955            1960                1965

Asn Glu Asn Ile His Ser Ile His Phe Ser Gly His Val Phe Thr
    1970            1975                1980

Val Arg Lys Lys Glu Glu Tyr Lys Met Ala Leu Tyr Asn Leu Tyr
    1985            1990                1995

Pro Gly Val Phe Glu Thr Val Glu Met Leu Pro Ser Lys Ala Gly
    2000            2005                2010

Ile Trp Arg Val Glu Cys Leu Ile Gly Glu His Leu His Ala Gly
    2015            2020                2025

Met Ser Thr Leu Phe Leu Val Tyr Ser Asn Lys Cys Gln Thr Pro
    2030            2035                2040

Leu Gly Met Ala Ser Gly His Ile Arg Asp Phe Gln Ile Thr Ala
    2045            2050                2055

Ser Gly Gln Tyr Gly Gln Trp Ala Pro Lys Leu Ala Arg Leu His
    2060            2065                2070

Tyr Ser Gly Ser Ile Asn Ala Trp Ser Thr Lys Glu Pro Phe Ser
    2075            2080                2085

Trp Ile Lys Val Asp Leu Leu Ala Pro Met Ile Ile His Gly Ile
    2090            2095                2100

Lys Thr Gln Gly Ala Arg Gln Lys Phe Ser Ser Leu Tyr Ile Ser
    2105            2110                2115

Gln Phe Ile Ile Met Tyr Ser Leu Asp Gly Lys Lys Trp Gln Thr
    2120            2125                2130

Tyr Arg Gly Asn Ser Thr Gly Thr Leu Met Val Phe Phe Gly Asn
    2135            2140                2145

Val Asp Ser Ser Gly Ile Lys His Asn Ile Phe Asn Pro Pro Ile
    2150            2155                2160

Ile Ala Arg Tyr Ile Arg Leu His Pro Thr His Tyr Ser Ile Arg
    2165            2170                2175

Ser Thr Leu Arg Met Glu Leu Met Gly Cys Asp Leu Asn Ser Cys
    2180            2185                2190

Ser Met Pro Leu Gly Met Glu Ser Lys Ala Ile Ser Asp Ala Gln
    2195            2200                2205

Ile Thr Ala Ser Ser Tyr Phe Thr Asn Met Phe Ala Thr Trp Ser
    2210            2215                2220

Pro Ser Lys Ala Arg Leu His Leu Gln Gly Arg Ser Asn Ala Trp
    2225            2230                2235

```
Arg Pro Gln Val Asn Asn Pro Lys Glu Trp Leu Gln Val Asp Phe
    2240                2245                2250

Gln Lys Thr Met Lys Val Thr Gly Val Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr
    2345                2350

<210> SEQ ID NO 2
<211> LENGTH: 2332
<212> TYPE: PRT
<213> ORGANISM: Homo sapiens

<400> SEQUENCE: 2

Ala Thr Arg Arg Tyr Tyr Leu Gly Ala Val Glu Leu Ser Trp Asp Tyr
  1               5                  10                  15

Met Gln Ser Asp Leu Gly Glu Leu Pro Val Asp Ala Arg Phe Pro Pro
                 20                  25                  30

Arg Val Pro Lys Ser Phe Pro Phe Asn Thr Ser Val Val Tyr Lys Lys
             35                  40                  45

Thr Leu Phe Val Glu Phe Thr Asp His Leu Phe Asn Ile Ala Lys Pro
         50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255
```

-continued

Val Ile Gly Met Gly Thr Thr Pro Glu Val His Ser Ile Phe Leu Glu
            260             265             270

Gly His Thr Phe Leu Val Arg Asn His Arg Gln Ala Ser Leu Glu Ile
        275             280             285

Ser Pro Ile Thr Phe Leu Thr Ala Gln Thr Leu Leu Met Asp Leu Gly
        290             295             300

Gln Phe Leu Leu Phe Cys His Ile Ser Ser His Gln His Asp Gly Met
305             310             315             320

Glu Ala Tyr Val Lys Val Asp Ser Cys Pro Glu Pro Gln Leu Arg
            325             330             335

Met Lys Asn Asn Glu Glu Ala Glu Asp Tyr Asp Asp Asp Leu Thr Asp
            340             345             350

Ser Glu Met Asp Val Val Arg Phe Asp Asp Asn Ser Pro Ser Phe
            355             360             365

Ile Gln Ile Arg Ser Val Ala Lys Lys His Pro Lys Thr Trp Val His
        370             375             380

Tyr Ile Ala Ala Glu Glu Asp Trp Asp Tyr Ala Pro Leu Val Leu
385             390             395             400

Ala Pro Asp Asp Arg Ser Tyr Lys Ser Gln Tyr Leu Asn Asn Gly Pro
            405             410             415

Gln Arg Ile Gly Arg Lys Tyr Lys Lys Val Arg Phe Met Ala Tyr Thr
            420             425             430

Asp Glu Thr Phe Lys Thr Arg Glu Ala Ile Gln His Glu Ser Gly Ile
        435             440             445

Leu Gly Pro Leu Leu Tyr Gly Glu Val Gly Asp Thr Leu Leu Ile Ile
    450             455             460

Phe Lys Asn Gln Ala Ser Arg Pro Tyr Asn Ile Tyr Pro His Gly Ile
465             470             475             480

Thr Asp Val Arg Pro Leu Tyr Ser Arg Arg Leu Pro Lys Gly Val Lys
            485             490             495

His Leu Lys Asp Phe Pro Ile Leu Pro Gly Glu Ile Phe Lys Tyr Lys
            500             505             510

Trp Thr Val Thr Val Glu Asp Gly Pro Thr Lys Ser Asp Pro Arg Cys
        515             520             525

Leu Thr Arg Tyr Tyr Ser Ser Phe Val Asn Met Glu Arg Asp Leu Ala
    530             535             540

Ser Gly Leu Ile Gly Pro Leu Leu Ile Cys Tyr Lys Glu Ser Val Asp
545             550             555             560

Gln Arg Gly Asn Gln Ile Met Ser Asp Lys Arg Asn Val Ile Leu Phe
            565             570             575

Ser Val Phe Asp Glu Asn Arg Ser Trp Tyr Leu Thr Glu Asn Ile Gln
            580             585             590

Arg Phe Leu Pro Asn Pro Ala Gly Val Gln Leu Glu Asp Pro Glu Phe
        595             600             605

Gln Ala Ser Asn Ile Met His Ser Ile Asn Gly Tyr Val Phe Asp Ser
            610             615             620

Leu Gln Leu Ser Val Cys Leu His Glu Val Ala Tyr Trp Tyr Ile Leu
625             630             635             640

Ser Ile Gly Ala Gln Thr Asp Phe Leu Ser Val Phe Phe Ser Gly Tyr
            645             650             655

Thr Phe Lys His Lys Met Val Tyr Glu Asp Thr Leu Thr Leu Phe Pro
            660             665             670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
            850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu
        1010                1015                1020

Asn Ser Pro Ser Val Trp Gln Asn Ile Leu Glu Ser Asp Thr Glu
        1025                1030                1035

Phe Lys Lys Val Thr Pro Leu Ile His Asp Arg Met Leu Met Asp
        1040                1045                1050

Lys Asn Ala Thr Ala Leu Arg Leu Asn His Met Ser Asn Lys Thr
        1055                1060                1065

Thr Ser Ser Lys Asn Met Glu Met Val Gln Gln Lys Lys Glu Gly
        1070                1075                1080

Pro Ile Pro Pro Asp Ala Gln Asn Pro Asp Met Ser Phe Phe Lys

-continued

```
             1085                1090                1095
Met Leu Phe Leu Pro Glu Ser Ala Arg Trp Ile Gln Arg Thr His
             1100                1105                1110
Gly Lys Asn Ser Leu Asn Ser Gly Gln Gly Pro Ser Pro Lys Gln
             1115                1120                1125
Leu Val Ser Leu Gly Pro Glu Lys Ser Val Glu Gly Gln Asn Phe
             1130                1135                1140
Leu Ser Glu Lys Asn Lys Val Val Val Gly Lys Gly Glu Phe Thr
             1145                1150                1155
Lys Asp Val Gly Leu Lys Glu Met Val Phe Pro Ser Ser Arg Asn
             1160                1165                1170
Leu Phe Leu Thr Asn Leu Asp Asn Leu His Glu Asn Asn Thr His
             1175                1180                1185
Asn Gln Glu Lys Lys Ile Gln Glu Glu Ile Glu Lys Lys Glu Thr
             1190                1195                1200
Leu Ile Gln Glu Asn Val Val Leu Pro Gln Ile His Thr Val Thr
             1205                1210                1215
Gly Thr Lys Asn Phe Met Lys Asn Leu Phe Leu Leu Ser Thr Arg
             1220                1225                1230
Gln Asn Val Glu Gly Ser Tyr Asp Gly Ala Tyr Ala Pro Val Leu
             1235                1240                1245
Gln Asp Phe Arg Ser Leu Asn Asp Ser Thr Asn Arg Thr Lys Lys
             1250                1255                1260
His Thr Ala His Phe Ser Lys Lys Gly Glu Glu Glu Asn Leu Glu
             1265                1270                1275
Gly Leu Gly Asn Gln Thr Lys Gln Ile Val Glu Lys Tyr Ala Cys
             1280                1285                1290
Thr Thr Arg Ile Ser Pro Asn Thr Ser Gln Gln Asn Phe Val Thr
             1295                1300                1305
Gln Arg Ser Lys Arg Ala Leu Lys Gln Phe Arg Leu Pro Leu Glu
             1310                1315                1320
Glu Thr Glu Leu Glu Lys Arg Ile Ile Val Asp Asp Thr Ser Thr
             1325                1330                1335
Gln Trp Ser Lys Asn Met Lys His Leu Thr Pro Ser Thr Leu Thr
             1340                1345                1350
Gln Ile Asp Tyr Asn Glu Lys Glu Lys Gly Ala Ile Thr Gln Ser
             1355                1360                1365
Pro Leu Ser Asp Cys Leu Thr Arg Ser His Ser Ile Pro Gln Ala
             1370                1375                1380
Asn Arg Ser Pro Leu Pro Ile Ala Lys Val Ser Ser Phe Pro Ser
             1385                1390                1395
Ile Arg Pro Ile Tyr Leu Thr Arg Val Leu Phe Gln Asp Asn Ser
             1400                1405                1410
Ser His Leu Pro Ala Ala Ser Tyr Arg Lys Lys Asp Ser Gly Val
             1415                1420                1425
Gln Glu Ser Ser His Phe Leu Gln Gly Ala Lys Lys Asn Asn Leu
             1430                1435                1440
Ser Leu Ala Ile Leu Thr Leu Glu Met Thr Gly Asp Gln Arg Glu
             1445                1450                1455
Val Gly Ser Leu Gly Thr Ser Ala Thr Asn Ser Val Thr Tyr Lys
             1460                1465                1470
Lys Val Glu Asn Thr Val Leu Pro Lys Pro Asp Leu Pro Lys Thr
             1475                1480                1485
```

-continued

```
Ser Gly Lys Val Glu Leu Leu Pro Lys Val His Ile Tyr Gln Lys
    1490                1495                1500

Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875
```

```
Phe Phe Thr Ile Phe Asp Glu Thr Lys Ser Trp Tyr Phe Thr Glu
         1880             1885             1890

Asn Met Glu Arg Asn Cys Arg Ala Pro Cys Asn Ile Gln Met Glu
         1895             1900             1905

Asp Pro Thr Phe Lys Glu Asn Tyr Arg Phe His Ala Ile Asn Gly
         1910             1915             1920

Tyr Ile Met Asp Thr Leu Pro Gly Leu Val Met Ala Gln Asp Gln
         1925             1930             1935

Arg Ile Arg Trp Tyr Leu Leu Ser Met Gly Ser Asn Glu Asn Ile
         1940             1945             1950

His Ser Ile His Phe Ser Gly His Val Phe Thr Val Arg Lys Lys
         1955             1960             1965

Glu Glu Tyr Lys Met Ala Leu Tyr Asn Leu Tyr Pro Gly Val Phe
         1970             1975             1980

Glu Thr Val Glu Met Leu Pro Ser Lys Ala Gly Ile Trp Arg Val
         1985             1990             1995

Glu Cys Leu Ile Gly Glu His Leu His Ala Gly Met Ser Thr Leu
         2000             2005             2010

Phe Leu Val Tyr Ser Asn Lys Cys Gln Thr Pro Leu Gly Met Ala
         2015             2020             2025

Ser Gly His Ile Arg Asp Phe Gln Ile Thr Ala Ser Gly Gln Tyr
         2030             2035             2040

Gly Gln Trp Ala Pro Lys Leu Ala Arg Leu His Tyr Ser Gly Ser
         2045             2050             2055

Ile Asn Ala Trp Ser Thr Lys Glu Pro Phe Ser Trp Ile Lys Val
         2060             2065             2070

Asp Leu Leu Ala Pro Met Ile Ile His Gly Ile Lys Thr Gln Gly
         2075             2080             2085

Ala Arg Gln Lys Phe Ser Ser Leu Tyr Ile Ser Gln Phe Ile Ile
         2090             2095             2100

Met Tyr Ser Leu Asp Gly Lys Lys Trp Gln Thr Tyr Arg Gly Asn
         2105             2110             2115

Ser Thr Gly Thr Leu Met Val Phe Phe Gly Asn Val Asp Ser Ser
         2120             2125             2130

Gly Ile Lys His Asn Ile Phe Asn Pro Pro Ile Ile Ala Arg Tyr
         2135             2140             2145

Ile Arg Leu His Pro Thr His Tyr Ser Ile Arg Ser Thr Leu Arg
         2150             2155             2160

Met Glu Leu Met Gly Cys Asp Leu Asn Ser Cys Ser Met Pro Leu
         2165             2170             2175

Gly Met Glu Ser Lys Ala Ile Ser Asp Ala Gln Ile Thr Ala Ser
         2180             2185             2190

Ser Tyr Phe Thr Asn Met Phe Ala Thr Trp Ser Pro Ser Lys Ala
         2195             2200             2205

Arg Leu His Leu Gln Gly Arg Ser Asn Ala Trp Arg Pro Gln Val
         2210             2215             2220

Asn Asn Pro Lys Glu Trp Leu Gln Val Asp Phe Gln Lys Thr Met
         2225             2230             2235

Lys Val Thr Gly Val Thr Thr Gln Gly Val Lys Ser Leu Leu Thr
         2240             2245             2250

Ser Met Tyr Val Lys Glu Phe Leu Ile Ser Ser Ser Gln Asp Gly
         2255             2260             2265

His Gln Trp Thr Leu Phe Phe Gln Asn Gly Lys Val Lys Val Phe
```

-continued

```
                2270                2275                2280

Gln Gly Asn Gln Asp Ser Phe Thr Pro Val Val Asn Ser Leu Asp
        2285                2290                2295

Pro Pro Leu Leu Thr Arg Tyr Leu Arg Ile His Pro Gln Ser Trp
        2300                2305                2310

Val His Gln Ile Ala Leu Arg Met Glu Val Leu Gly Cys Glu Ala
        2315                2320                2325

Gln Asp Leu Tyr
        2330
```

POLYMER-FACTOR VIII MOIETY CONJUGATES

CROSS REFERENCE TO RELATED APPLICATIONS

This application is a continuation of U.S. patent application Ser. No. 14/517,679, filed Oct. 17, 2014, now abandoned, which is a continuation of U.S. patent application Ser. No. 13/431,844, filed Mar. 27, 2012, now U.S. Pat. No. 8,889,831, which is a continuation of U.S. patent application Ser. No. 12/636,594, filed Dec. 11, 2009, now U.S. Pat. No. 8,247,536, which is a continuation of U.S. patent application Ser. No. 11/702,302, filed Feb. 5, 2007, now U.S. Pat. No. 7,858,749, which is a continuation of U.S. patent application Ser. No. 10/789,956, filed Feb. 26, 2004, now U.S. Pat. No. 7,199,223, which claims the benefit of priority to U.S. Provisional Patent Application Ser. No. 60/450,578, filed Feb. 26, 2003, all of which are incorporated herein by reference.

FIELD OF THE INVENTION

The present invention relates generally to conjugates comprising a Factor VIII moiety (i.e., a moiety having Factor VIII activity) and a polymer. In addition, the invention relates to compositions comprising the conjugates, methods for synthesizing the conjugates, and methods for treating patients.

REFERENCE TO SEQUENCE LISTING, TABLE OR COMPUTER PROGRAM

A Sequence Listing is being submitted electronically via EFS in the form of a text file, created Dec. 8, 2015 and named "0915340428seqlist.txt" (41122 bytes), the contents of which are incorporated herein by reference in their entirety.

BACKGROUND OF THE INVENTION

Hemostasis is the process of arresting the outflow of blood from an injured blood vessel. For mammals, as well as many other organisms, the hemostatic process is critically important for continued survival. Defects in the hemostatic process can result in, for example, the inability to effectively form blood clots that serve to stop the loss of blood following vascular injury. In humans, individuals who suffer from an inability to form blood clots are called hemophiliacs. Of particular concern for hemophiliacs is the life-threatening risk that once started, bleeding will never cease.

Generally, hemophiliacs lack the ability to produce effective amounts of one or more substances required to form blood clots. For example, hemophiliacs who suffer from hemophilia A (also called "classic hemophilia") have an inability to produce effective levels of Factor VIII (also known as "antihemophilia factor A," "antihemophilic globulin," and "AHG"). Factor VIII is a key component of one of several "cascades" of reactions that result in the formation of blood clots. Critical for the cascade of reactions referred to as the "intrinsic pathway," Factor VIII ultimately influences the conversion of fibrinogen into the major component of blood clots, fibrin.

Although the intrinsic pathway of blood clot formation is relatively complex, the role of Factor VIII can be described briefly. In the presence of relatively small amounts of thrombin (released, for example, by the cells of ruptured tissues), Factor VIII is converted into its activated form known as Factor VIIIa. Factor VIIIa (along with other substances), in turn, activates another factor, Factor X into Factor Xa. Thereafter, Factor Xa (along with other substances) converts prothrombin into thrombin, with the result that a relatively large amount of thrombin is produced over time. Relatively large amounts of thrombin effectively convert fibrinogen into fibrin. Fibrin, in turn, forms the matrix or lattice responsible for the formation of blood clots. Factor VIII's role in the intrinsic pathway of blood clotting is shown in FIG. 6.

Affecting one or two males for every 10,000 live births in all populations, hemophilia A can result from any one of a variety of mutations of the Factor VIII gene, which is located on the X-chromosome. Depending on the particular mutation, hemophilia A can manifest itself as severe, moderate or mild. Individuals suffering from the severest forms of hemophilia A entirely lack the ability to express active forms of Factor VIII. Clinically, individuals affected with hemophilia A suffer from muscle hemorrhage, joint hemorrhage, easy bruising, and prolonged bleeding from wounds. The mean age of individuals suffering from hemophilia A without treatment is twenty. Current treatment of hemophilia A involves the infusion of exogenous Factor VIII concentrate collected from human plasma or prepared via recombinant DNA techniques. Because these treatments serve only to supplement the lack of effective levels of Factor VIII, individuals suffering from Factor VIII require regular injections of Factor VIII concentrate throughout their lives.

Several commercial forms of Factor VIII concentrates are available to provide replacement therapy for patients suffering from hemophilia A. For example, blood-derived Factor VIII concentrate products are sold under the HEMOFIL® M, Antihemophilic Factor VIII (human) (Baxter, Deerfield, Ill.), KOATE® DVI, Antihemophilic Factor VIII (human) (Bayer, Research Tringle Park, N.C.), MONARC-M™, Antihemophilic Factor VIII (human) (American Red Cross, Washington, D.C.), and MONOCLATE P®, Antihemophilic Factor VIII (human) (Aventis, Bridgewater, N.J.) brands. With respect to recombinantly prepared Factor VIII concentrates, commercial products are provided under the HELIXATE® FS, Factor VIII, recombinant (Aventis, Bridgewater, N.J.), KOGENATE FS®, Factor VIII, recombinant (Bayer, Research Triangle Park, N.C.), RECOMBINATE®, Factor VIII, recombinant (Baxter, Deerfield, Ill.), ADVATE®, Factor VIII, recombinant (Baxter, Deerfield, Ill.), and REFACTO®, Factor VIII, recombinant (Wyeth/Genetics Institute, Cambridge, Mass.) brands.

Generally, recombinant sources of Factor VIII concentrates are favored over blood-derived sources since the latter involves the risk of transmitting viruses and/or other diseases associated with blood donation. While recombinant-based formulations avoid these drawbacks, the processing of recombinant-based products often requires the presence of certain proteins such as albumin, which are inevitably present in the final formulation administered to the patient. Often, patients who receive such formulations develop allergic reactions to these foreign proteins. In any event, both blood-derived and recombinant-based products suffer from the disadvantage of repeated administration.

PEGylation, or the attachment of a poly(ethylene glycol) derivative to a protein, has been described as a means to reduce immunogenicity as well as a means to prolong a protein's in vivo half-life. With respect to Factor VIII, however, previous experiences with forming protein-polymer conjugates has proven to be of little predictive value vis-à-vis polymer coupling to Factor VIII. See U.S. Pat. No. 4,970,300.

Notwithstanding these difficulties, attempts of preparing satisfactory compositions of conjugates of certain polymers to Factor VIII have been described. For example, previously referenced U.S. Pat. No. 4,970,300 describes the PEGylation of Factor VIII using a specific poly(ethylene glycol) derivative having a molecular weight within the range of about 500 to 5,000. In addition, U.S. Pat. No. 6,048,720 describes efficient protection against degradation in an in vitro environment when four to five monomethoxy poly(ethylene glycol) strands are conjugated to Factor VIII.

None of these described conjugates, however, has proven to satisfactorily address the problems associated with current Factor VIII-based therapies. For example, conjugates comprised of relatively small polymers (e.g., of about 5,000 Daltons or less) may not suitably provide extended in vivo half-life and/or sufficiently reduced immune response. In addition, conjugates having many individual polymers attached to Factor VIII are more likely to have reduced activity as a result of the polymer(s) blocking sites necessary for activity.

Thus, there remains a need in the art to provide additional conjugates between water-soluble polymers and moieties having Factor VIII activity. The present invention is therefore directed to such conjugates as well as compositions comprising the conjugates and related methods as described herein, which are believed to be new and completely unsuggested by the art.

SUMMARY OF THE INVENTION

Accordingly, it is a primary object of this invention to provide a composition comprising a plurality of conjugates, preferably although not necessarily, each having one to three water-soluble polymers covalently attached to a Factor VIII moiety, wherein each water-soluble polymer preferably has a nominal average molecular weight in the range of greater than 5,000 Daltons to about 100,000 Daltons.

It is another object of the invention to provide such a conjugate wherein each of the water-soluble polymers is a poly(alkylene oxide).

It is an additional object of the invention to provide such a conjugate wherein each of the water-soluble polymers is a poly(ethylene glycol).

It is a further object of the invention to provide a conjugate comprising a plurality of monoPEGylated Factor VIII moiety conjugates.

It is still a further object of the invention to provide a method for preparing polymer conjugates comprising the steps of contacting one or more activated, water-soluble polymers to a Factor VIII moiety under conditions sufficient to result in a plurality of conjugates, preferably although not necessarily, each having one to three water-soluble polymers covalently attached to a Factor VIII moiety, wherein the water-soluble polymer preferably has a nominal average molecular weight in the range of greater than 5,000 Daltons to about 150,000 Daltons.

It is an additional object of the invention to provide a method for treating a patient in need of Factor VIII therapy, comprising the step of administering to the patient a composition as described herein, wherein the composition contains a therapeutically effective amount of one or more of the conjugates.

It is still yet an additional object of the invention to provide a method for preparing a water-soluble polymer-Factor VIII moiety conjugate comprising the step of contacting, under conjugation conditions, a Factor VIII moiety with a polymeric reagent.

Additional objects, advantages and novel features of the invention will be set forth in the description that follows, and in part, will become apparent to those skilled in the art upon reading the following, or may be learned by practice of the invention.

In one embodiment then, a composition is provided comprising a plurality of conjugates, preferably although not necessarily, each having one to three-water soluble polymers covalently attached to a Factor VIII moiety, wherein each water-soluble polymer preferably has a nominal average molecular weight in the range of greater than 5,000 Daltons to about 150,000 Daltons. Although any Factor VIII moiety can be used, it is preferred that the compositions comprise Factor VIII per se (as described in, for example, U.S. Pat. No. 4,757,006), Factor VIIIa (i.e., the activated form of Factor VIII produced when Factor VIII is placed in contact with relatively small amounts of thrombin), Factor VIII: vWF (i.e., Factor VIII bound to von Willebrand Factor), and/or truncated versions of Factor VIII such as B-domain deleted Factor VIII (as described in, for example, U.S. Pat. No. 4,868,112).

The polymer(s) can be any water-soluble polymer and the invention is not limited in this regard. It is preferred, however, that each polymer present in the conjugate is selected from the group consisting of poly(alkylene oxide), poly(vinyl pyrrolidone), poly(vinyl alcohol), polyoxazoline, poly(acryloylmorpholine), and combinations thereof. It is particularly, preferred, however, that a poly(alkylene oxide) such as a poly(ethylene glycol) derivative is used as the polymer in the present invention.

The conjugates described herein advantageously reduce immunogenicity, a problem encountered by many hemophiliacs treated with exogenous sources of Factor VIII. In addition, the present conjugates require decreased frequency of dosing compared to Factor VIII compositions lacking conjugates. By reducing the frequency of dosing, the conjugates advantageously decrease the number of painful injections hemophiliacs must endure in order to provide sustained levels of an agent having Factor VIII activity.

In another embodiment, a method for preparing a conjugate is provided. The method comprises the step of contacting one or more activated, water-soluble polymers (i.e., a polymeric reagent) preferably having a nominal average molecular weight in the range of greater than 5,000 Daltons to about 150,000 Daltons to a Factor VIII moiety. Activation of the water-soluble polymer can be accomplished under any art-known method so long as the resulting polymer, under the proper conditions of pH, temperature, and so forth, will form a covalent bond such that the Factor VIII moiety is covalently attached to the polymer. Contacting of the one or more activated, water-soluble polymers to the Factor VIII moiety is carried out under those conditions required for the activated, water-soluble polymer to form a covalent attachment at the desired site in the moiety. The method results in a plurality of conjugates, preferably although not necessarily, each having one to three water-soluble polymers covalently attached to the Factor VIII moiety. In some instances, the conjugate can comprise a single polymer attached to two, three, four, five, six, seven, eight, or more Factor VIII moieties. Optionally, the resulting composition can be further processed in order remove undesired species such as, for example, conjugates having an undesired number of polymers. In order to remove such undesired species, purification techniques such as size-exclusion chromatography can be used.

In still another embodiment of the invention, compositions are provided comprising a conjugate of the invention in combination with a pharmaceutically acceptable excipient. The compositions encompass all types of formulations and in particular those that are suited for injection such as powders that can be reconstituted, as well as liquids (e.g., suspensions and solutions).

In an additional embodiment of the invention, a method of administering the conjugate is provided. The method of administering comprises the step of administering to the patient a composition as described herein, wherein the composition contains a therapeutically effective amount of the conjugate. Typically, the step of administering the conjugate-containing composition is effected by injection (e.g., intramuscular injection, intravenous injection, subcutaneous injection, and so forth).

DETAILED DESCRIPTION OF THE INVENTION

Figure 1:
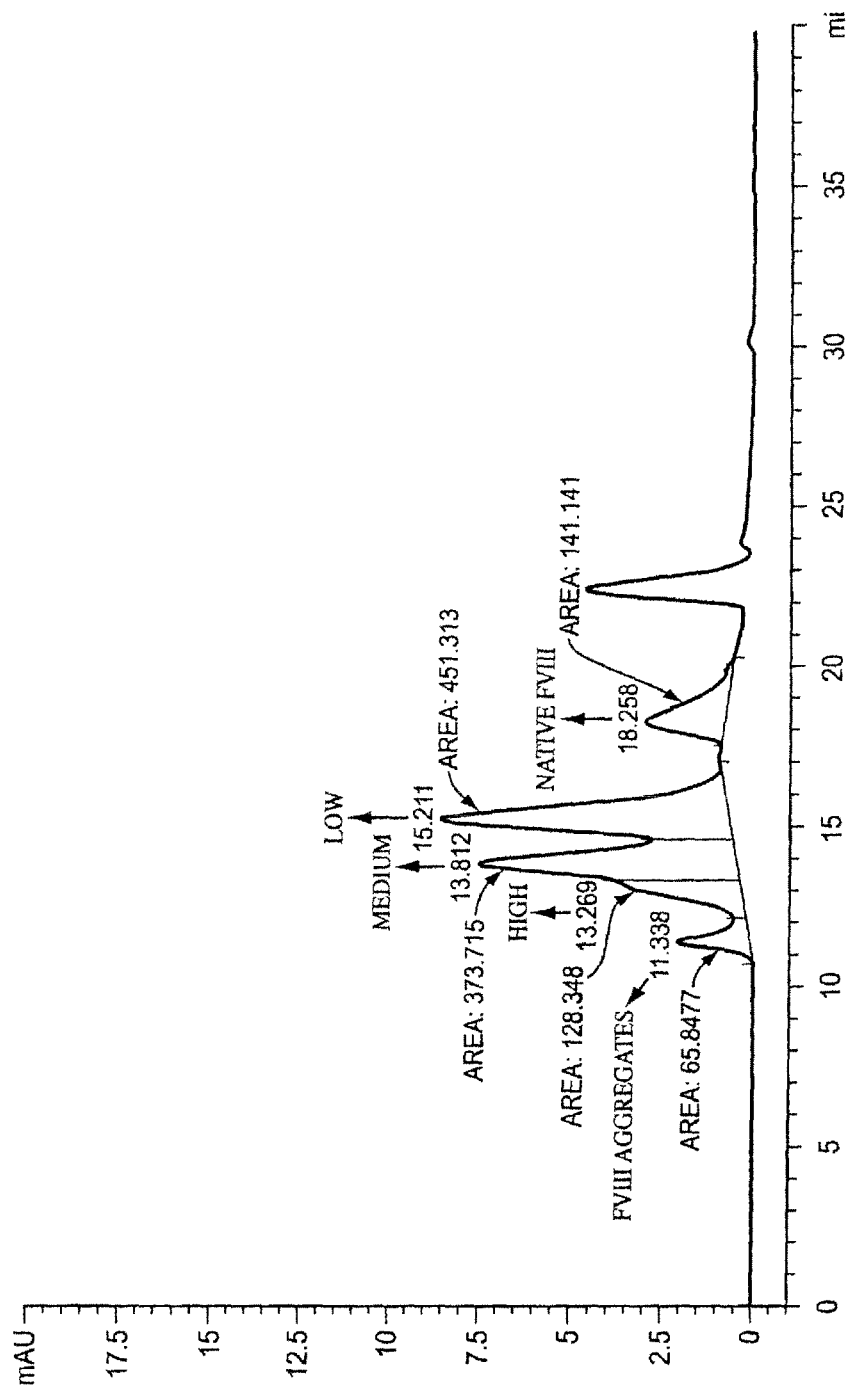
FIG. 1 is a SEC plot corresponding to the reaction mixture formed upon pegylation of B-Domain deleted Factor VIII with mPEG-SPA, 30K, as described in Example 6.

Before describing the present invention in detail, it is to be understood that this invention is not limited to the particular polymers, synthetic techniques, Factor VIII moieties, and the like, as such may vary.

It must be noted that, as used in this specification and the intended claims, the singular forms "a," "an," and "the" include plural referents unless the context clearly dictates otherwise. Thus, for example, reference to "a polymer" includes a single polymer as well as two or more of the same or different polymers, reference to a "an optional excipient" refers to a single optional excipient as well as two or more of the same or different optional excipients, and the like.

In describing and claim1ng the present invention, the following terminology will be used in accordance with the definitions described below.

"PEG," "polyethylene glycol" and "poly(ethylene glycol)" as used herein, are interchangeable and meant to encompass any water-soluble poly(ethylene oxide). Typically, PEGs for use in accordance with the invention comprise the following structure "—$(OCH_2CH_2)_n$—" where (n) is 2 to 4000. As used herein, PEG also includes "—$CH_2CH_2$—$O(CH_2CH_2O)_n$—$CH_2CH_2$—" and "—$(OCH_2CH_2)_nO$—," depending upon whether or not the terminal oxygens have been displaced. Throughout the specification and claims, it should be remembered that the term "PEG" includes structures having various terminal or "end capping" groups and so forth. The term "PEG" also means a polymer that contains a majority, that is to say, greater than 50%, of —$OCH_2CH_2$— repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or endpoint of a polymer having an end-capping moiety. Typically, although not necessarily, the end-capping moiety comprises a hydroxy or $C_{1-20}$ alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in $CH_3(OCH_2CH_2)_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer as described herein, means a polymer that in its entirety is not found in nature. A non-naturally occurring polymer of the invention may, however, contain one or more monomers or segments of monomers that are naturally occurring, so long as the overall polymer structure is not found in nature.

The term "water soluble" as in a "water-soluble polymer" polymer is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water.

It is most preferred, however, that the water-soluble polymer is about 95% (by weight) soluble in water or completely soluble in water.

"Nominal average molecular weight" in the context of a water-soluble, non-naturally occurring polymer such as PEG, refers to the mass average molecular weight of the polymer, typically determined by size-exclusion chromatography, MALDI (matrix assisted laser desorption/ionization), light scattering techniques, or intrinsic velocity determination in 1,2,4-trichlorobenzene. The polymers are typically polydisperse, possessing low polydispersity values of preferably less than about 1.2, more preferably less than about 1.15, still more preferably less than about 1.10, yet still more preferably less than about 1.05, and most preferably less than about 1.03.

The term "active" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "linkage" or "linker" are used herein to refer to an atom or a collection of atoms optionally used to link interconnecting moieties such as a terminus of a polymer segment and a Factor VIII moiety or an electrophile or nucleophile of a Factor VIII moiety. The linker of the invention may be hydrolytically stable or may include a physiologically hydrolyzable or enzymatically degradable linkage.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

"Electrophile" and "electrophilic group" refer to an ion or atom or collection of atoms, that may be ionic, having an electrophilic center, i.e., a center that is electron seeking, capable of reacting with a nucleophile.

"Nucleophile" and "nucelophilic group" refers to an ion or atom or collection of atoms that may be ionic having a nucleophilic center, i.e., a center that is seeking an electrophilic center or with an electrophile.

A "physiologically cleavable" or "hydrolysable" or "degradable" bond is a bond that reacts with water (i.e., is hydrolyzed) under physiological conditions. Preferred are bonds that have a hydrolysis half-life at pH 8, 25° C. of less than about 30 minutes. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient or carrier" refers to an excipient that may optionally be included in the compositions of the invention and that causes no significant adverse toxicological effects to the patient. "Pharmacologically effective amount," "physiologically effective amount," and "therapeutically effective amount" are used interchangeably herein to mean the amount of a polymer-Factor VIII moiety conjugate that is needed to provide a desired level of the conjugate (or corresponding unconjugated Factor VIII moiety) in the bloodstream or in the target tissue. The precise amount will depend upon numerous factors, e.g., the particular Factor VIII moiety, the components and physical characteristics of the therapeutic composition, intended patient population, individual patient considerations, and the like, and can readily be determined by one skilled in the art, based upon the information provided herein.

"Multi-functional" means a polymer having 3 or more functional groups contained therein, where the functional groups may be the same or different. Multi-functional polymeric reagents of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

The term "Factor VIII moiety," as used herein, refers to a moiety having Factor VIII activity. The Factor VIII moiety will also have at least one electrophilic group or nucleophilic group suitable for reaction with a polymeric reagent. Typically, although not necessarily, the Factor VIII moiety is a protein. In addition, the term "Factor VIII moiety" encompasses both the Factor VIII moiety prior to conjugation as well as the Factor VIII moiety residue following conjugation. As will be explained in further detail below, one of ordinary skill in the art can determine whether any given moiety has Factor VIII activity.

The term "patient," refers to a living organism suffering from or prone to a condition that can be prevented or treated by administration of an active agent (e.g., conjugate), and includes both humans and animals.

"Optional" or "optionally" means that the subsequently described circumstance may or may not occur, so that the description includes instances where the circumstance occurs and instances where it does not.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

Turning to a first embodiment of the invention then, a composition is provided comprising a plurality of conjugates, preferably although not necessarily, each having one to three water-soluble polymers covalently attached to a Factor VIII moiety, wherein each of the water-soluble polymers preferably has a nominal average molecular weight in the range of greater than 5,000 Daltons to about 150,000 Daltons.

Native Factor VIII is a 2,351 amino acid, single chain glycoprotein that is structurally organized as A1-A2-B-A3-C1-C2. The expressed 2,351 amino acid sequence is provided as SEQ ID NO:1. When the expressed polypeptide is translocated into the lumen of the endoplasmic reticulum, however, a 19-amino acid signal sequence is cleaved, resulting in a second sequence. This second sequence, herein provided as SEQ ID NO:2, lacks the leading 19 amino acids is conventionally used by researchers to assign a numeric location (e.g., $Arg^{372}$) to a given amino acid residue of Factor VIII. Thus, unless specifically noted, all assignments of a numeric location of an amino acid residue as provided herein are based on SEQ ID NO:2.

In the presence of relatively small amounts of thrombin, Factor VIII is cleaved by thrombin at $Arg^{372}$, $Arg^{740}$, and $Arg^{1689}$ to produce Factor VIIIa. Factor VIIIa is a heterotrimer comprised of the A1 subunit bound (via a copper ion) to the thrombin-cleaved light chain A3-C1-C2 and the free A2 subunit bound via ionic interactions to A1. It will be appreciated that a Factor VIII moiety is not limited to merely "active" forms of Factor VIII (e.g., Factor VIIIa) and that the term "Factor VIII moiety" encompasses "precursor" forms as well as other substances that having a similar procoagulant effect.

For any given moiety, it is possible to determine whether that moiety has Factor VIII activity. For example, several animal lines have been intentionally bred with the genetic mutation for hemophilia such that an animal produced from such a line has very low and insufficient levels of Factor VIII. Such lines are available from a variety of sources such as, without limitation, the Division of Laboratories and Research, New York Department of Public Health, Albany, N.Y. and the Department of Pathology, University of North Carolina, Chapel Hill, N.C. Both of these sources, for example, provide canines suffering from canine hemophilia A. In order to test the Factor VIII activity of any given moiety in question, the moiety is injected into the diseased animal, a small cut made and bleeding time compared to a healthy control. Another method useful for determining Factor VIII activity is to determine cofactor and procoagulant activity. See, for example, Mertens et al. (1993) *Brit. J Haematol.* 85:133-42. Other methods known to those of ordinary skill in the art can also be used to determine whether a given moiety has Factor VIII activity. Such methods are useful for determining the Factor VIII activity of both the moiety itself (and therefore can be used as a "Factor VIII moiety") as well as the corresponding polymer-moiety conjugate.

Nonlimiting examples of Factor VIII moieties include the following: Factor VIII; Factor VIIIa; Factor VIII:C; Factor VIII:vWF; B-domain deleted Factor VIII (and other truncated versions of Factor VIII); hybrid proteins, such as those described in U.S. Pat. No. 6,158,888; glycosylated proteins having Factor VIII activity, such as those described in U.S. Patent Application Publication No. US2003/0077752; and peptide mimetics having Factor VIII activity. Preferred truncated Factor VIII versions (encompassed by the term "B-domain" deleted Factor VIII) corresponds to a protein having the amino acid sequence of human Factor VIII (SEQ ID NO:1) having a deletion corresponding to at least 581 amino acids within the region between $Arg^{759}$ and $Ser^{1709}$, more preferably wherein the deletion corresponds to one of the region between $Pro^{1000}$ and $Asp^{1582}$, the region between $Thr^{778}$ and $Pro^{1659}$, and the region between $Thr^{778}$ and $Glu^{1694}$. Biologically active fragments, deletion variants, substitution variants or addition variants of any of the foregoing that maintain at least some degree of Factor VIII activity can also serve as a Factor VIII moiety.

The moiety having Factor VIII activity can advantageously be modified to include one or more amino acid residues such as, for example, lysine, cysteine and/or arginine, in order to provide facile attachment of the polymer to an atom within the side chain of the amino acid. Techniques for adding amino acid residues are well known to those of ordinary skill in the art. Reference is made to J. March, Advanced Organic Chemistry: Reactions Mechanisms and Structure, 4th Ed. (New York: Wiley-Interscience, 1992).

The Factor VIII moiety can be obtained from blood-derived sources. For example, Factor VIII can be fractionated from human plasma using precipitation and centrifugation techniques known to those of ordinary skill in the art. See, for example, Wickerhauser (1976) *Transfusion* 16(4): 345-350 and Slichter et al. (1976) *Transfusion* 16(6):616-

626. Factor VIII can also be isolated from human granulocytes. See Szmitkoski et al. (1977) *Haematologia (Budap)* 11(1-2):177-187.

In addition, the Factor VIII moiety can also be obtained from recombinant methods. Briefly, recombinant methods involve constructing the nucleic acid encoding the desired polypeptide or fragment, cloning the nucleic acid into an expression vector, transforming a host cell (e.g., bacteria, yeast, or mammalian cell such as Chinese hamster ovary cell or baby hamster kidney cell), and expressing the nucleic acid to produce the desired polypeptide or fragment. Methods for producing and expressing recombinant polypeptides in vitro and in prokaryotic and eukaryotic host cells are known to those of ordinary skill in the art. See, for example, U.S. Pat. No. 4,868,122.

To facilitate identification and purification of the recombinant polypeptide, nucleic acid sequences that encode for an epitope tag or other affinity binding sequence can be inserted or added in-frame with the coding sequence, thereby producing a fusion protein comprised of the desired polypeptide and a polypeptide suited for binding. Fusion proteins can be identified and purified by first running a mixture containing the fusion protein through an affinity column bearing binding moieties (e.g., antibodies) directed against the epitope tag or other binding sequence in the fusion proteins, thereby binding the fusion protein within the column. Thereafter, the fusion protein can be recovered by washing the column with the appropriate solution (e.g., acid) to release the bound fusion protein. The recombinant polypeptide can also be identified and purified by lysing the host cells, separating the polypeptide, e.g., by size exclusion chromatography, and collecting the polypeptide. These and other methods for identifying and purifying recombinant polypeptides are known to those of ordinary skill in the art.

The compositions of the invention can comprise a plurality of conjugates, each conjugate comprised of the same Factor VIII moiety (i.e., within the entire composition, only one type of Factor VIII moiety is found). In addition, the composition can comprise a plurality of conjugates wherein any given conjugate is comprised of a moiety selected from the group consisting of two or more different Factor VIII moieties (i.e., within the entire composition, two or more different Factor VIII moieties are found). Optimally, however, substantially all of the plurality of conjugates in the composition (e.g., 85% or more of the plurality of conjugates in the composition) are each comprised of the same Factor VIII moiety.

Moreover, it is preferred that the composition containing the conjugates is free or substantially free from albumin. It is also preferred that the composition is free or substantially free of proteins that do not have Factor VIII activity. Thus, it is preferred that the composition is 85%, more preferably 95%, and most preferably 99% free from albumin. Additionally, it is preferred that the composition is 85%, more preferably 95%, and most preferably 99% free from any protein that does not have Factor VIII activity.

As previously discussed, each conjugate comprises a Factor VIII moiety attached to a water-soluble polymer. With respect to the water-soluble polymer, the water-soluble polymer is nonpeptidic, nontoxic, non-naturally occurring and biocompatible. With respect to biocompatibility, a substance is considered biocompatible if the beneficial effects associated with use of the substance alone or with another substance (e.g., active agent such a Factor VIII moiety) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water-soluble polymer is biocompatible and nonimmunogenic.

Further the polymer is typically characterized as having from 2 to about 300 termini. Examples of such polymers include, but are not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), and combinations of any of the foregoing.

The polymer is not limited in a particular structure and can be linear (e.g., alkoxy PEG or bifunctional PEG), branched or multi-armed (e.g., forked PEG or PEG attached to a polyol core), dendritic, or with degradable linkages. Moreover, the internal structure of the polymer can be organized in any of number of different patterns and can be selected from the group consisting of homopolymer, alternating copolymer, random copolymer, block copolymer, alternating tripolymer, random tripolymer, and block tripolymer.

Typically, PEG and other water-soluble polymers are activated with a suitable activating group appropriate for coupling to a desired site on the Factor VIII moiety. An activated polymeric reagent will possess a reactive group for reaction with the Factor VIII moiety. Representative polymeric reagents and methods for conjugating these polymers to an active moiety are known in the art and further described in Zalipsky, S., et al., "*Use of Functionalized Poly(Ethylene Glycols) for Modification of Polypeptides*" in Polyethylene Glycol Chemistry: Biotechnical and Biomedical Applications, J. M. Harris, Plenus Press, New York (1992), and in Zalipsky (1995) *Advanced Drug Reviews* 16:157-182.

Typically, the nominal average molecular weight of any given polymer in the conjugate is from about 100 Daltons to about 150,000 Daltons. Exemplary ranges, however, include nominal average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of from about 20,000 Daltons to about 85,000 Daltons, and in the range of from about 53,000 Daltons to about 85,000 Daltons. For any given water-soluble polymer, PEGs having these molecular weight ranges are preferred.

Exemplary nominal average molecular weights for the water-soluble polymer segment include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 40,000 Daltons, about 50,000 Daltons, about 60,000 Daltons, and about 75,000 Daltons.

When used as the polymer, PEGs will typically comprise a number of (OCH$_2$CH$_2$) monomers. As used throughout the description, the number of repeating units is identified by the subscript "n" in "(OCH$_2$CH$_2$)$_n$." Thus, the value of (n) typically falls within one or more of the following ranges: from 2 to about 2,300, from about 100 to about 2,300, from about 135 to about 2,000, from about 230 to about 1,900, from about 450 to about 1,900, and from about 1,200 to about 1,900. For any given polymer in which the molecular weight is known, it is possible to determine the number of repeating units (i.e., "n") by dividing the total molecular weight of the polymer by the molecular weight of the repeating unit.

One particularly preferred polymer for use in the invention is an end-capped polymer, that is, a polymer having at least one terminus capped with a relatively inert group, such as a lower C$_{1-6}$ alkoxy group. When the polymer is PEG, for example, it is preferred to use a methoxy-PEG (commonly referred to as mPEG), which is a linear form of PEG wherein one terminus of the polymer is a methoxy (—OCH$_3$) group, while the other terminus is a hydroxyl or other functional group that can be optionally chemically modified.

In one form useful in the present invention, free or unbound PEG is a linear polymer terminated at each end with hydroxyl groups:

wherein (m') typically ranges from zero to about 4,000.

The above polymer, alpha-, omega-dihydroxylpoly(ethylene glycol), can be represented in brief form as HO-PEG-OH where it is understood that the -PEG- symbol can represent the following structural unit:

wherein (m') is as defined as above.

Another type of PEG useful in the present invention is methoxy-PEG-OH, or mPEG in brief, in which one terminus is the relatively inert methoxy group, while the other terminus is a hydroxyl group. The structure of mPEG is given below.

wherein (m') is as described above.

Multi-armed or branched PEG molecules, such as those described in U.S. Pat. No. 5,932,462, can also be used as the PEG polymer. For example, PEG can have the structure:

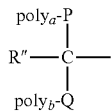

wherein:
poly$_a$ and poly$_b$ are PEG backbones (either the same or different), such as methoxy poly(ethylene glycol);
R" is a nonreactive moiety, such as H, methyl or a PEG backbone; and
P and Q are nonreactive linkages. In a preferred embodiment, the branched PEG polymer is methoxy poly(ethylene glycol) disubstituted lysine. Depending on the specific Factor VIII moiety used, the reactive ester functional group of the disubstituted lysine may be further modified to form a functional group suitable for reaction with the target group within the Factor VIII moiety.

These polymers may be linear, or may be in any of the above-described forms.

In addition, the PEG can comprise a forked PEG. An example of a forked PEG is represented by the following structure:

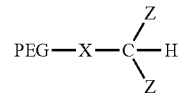

wherein: X is a spacer moiety of one or more atoms and each Z is an activated terminal group linked to CH by a chain of atoms of defined length. International Application No. PCT/US99/05333, discloses various forked PEG structures capable of use in the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or degradable linkages in the polymer, including any of the above described polymers. For example, PEG can be prepared with ester linkages in the polymer that are subject to hydrolysis. As shown below, this hydrolysis results in cleavage of the polymer into fragments of lower molecular weight:

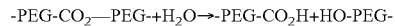

Other hydrolytically degradable linkages, useful as a degradable linkage within a polymer backbone, include: carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

Such optional features of the polymer conjugate, i.e., the introduction of one or more degradable linkages into the polymer chain, may provide for additional control over the final desired pharmacological properties of the conjugate upon administration. For example, a large and relatively inert conjugate (i.e., having one or more high molecular weight PEG chains attached thereto, for example, one or more PEG chains having a molecular weight greater than about 10,000, wherein the conjugate possesses essentially no bioactivity) may be administered, which is hydrolyzed to generate a bioactive conjugate possessing a portion of the original PEG chain. In this way, the properties of the conjugate can be more effectively tailored to balance the bioactivity of the conjugate over time.

Those of ordinary skill in the art will recognize that the foregoing discussion concerning substantially water-soluble polymer segments is by no means exhaustive and is merely illustrative, and that all polymeric materials having the qualities described above are contemplated. As used herein, the term "polymeric reagent" generally refers to an entire molecule, which can comprise a water-soluble polymer segment and a functional group.

As described above, a conjugate of the invention comprises a water-soluble polymer covalently attached to a Factor VIII moiety. Typically, for any given conjugate, there will be one to three water-soluble polymers covalently attached to one or more moieties having Factor VIII activity. In some instances, however, the conjugate may have 1, 2, 3, 4, 5, 6, 7, 8 or more water-soluble polymers individually attached to a Factor VIII moiety.

The particular linkage within the moiety having Factor VIII activity and the polymer depends on a number of factors. Such factors include, for example, the particular linkage chemistry employed, the particular moiety having Factor VIII activity, the available functional groups within the moiety having Factor VIII activity (either for attachment to a polymer or conversion to a suitable attachment site), the possible presence of additional reactive functional groups within the moiety having Factor VIII activity, and the like.

The conjugates of the invention can be, although not necessarily, prodrugs, meaning that the linkage between the polymer and the Factor VIII moiety is hydrolytically degradable to allow release of the parent moiety. Exemplary degradable linkages include carboxylate ester, phosphate ester, thiolester, anhydrides, acetals, ketals, acyloxyalkyl ether, imines, orthoesters, peptides and oligonucleotides. Such linkages can be readily prepared by appropriate modification of either the Factor VIII moiety (e.g., the carboxyl group C terminus of the protein or a side chain hydroxyl group of an amino acid such as serine or threonine contained within the protein) and/or the polymeric reagent using coupling methods commonly employed in the art. Most preferred, however, are hydrolyzable linkages that are readily formed by reaction of a suitably activated polymer with a non-modified functional group contained within the moiety having Factor VIII activity.

Alternatively, a hydrolytically stable linkage, such as an amide, urethane (also known as carbamate), amine, thioether (also known as sulfide), or urea (also known as carbamide) linkage can also be employed as the linkage for coupling the Factor VIII moiety. In some cases, however, it is preferred that the linkage is not a carbamate linkage and not a carbamide linkage, and furthermore, that no linkage is formed based on the reaction of a polymer derivative bearing an isocyanate or isothiocyanate species to a Factor VIII moiety. Again, a preferred hydrolytically stable linkage is an amide. An amide can be readily prepared by reaction of a carboxyl group contained within the Factor VIII moiety (e.g., the terminal carboxyl of a peptidic moiety having Factor VIII activity) with an amino-terminated polymer.

The conjugates (as opposed to an unconjugated Factor VIII moiety) may or may not possess a measurable degree of Factor VIII activity. That is to say, a polymer conjugate in accordance with the invention will possesses anywhere from about 0.1% to about 100% or more of the bioactivity of the unmodified parent Factor VIII moiety. Preferably, compounds possessing little or no Factor VIII activity typically contain a hydrolyzable linkage connecting the polymer to the moiety, so that regardless of the lack of activity in the conjugate, the active parent molecule (or a derivative thereof) is released upon aqueous-induced cleavage of the hydrolyzable linkage. Such activity may be determined using a suitable in-vivo or in-vitro model, depending upon the known activity of the particular moiety having Factor VIII activity employed.

For conjugates possessing a hydrolytically stable linkage that couples the moiety having Factor VIII activity to the polymer, the conjugate will typically possess a measurable degree of specific activity. For instance, such polymer conjugates are typically characterized as having an activity of at least about 2%, 5%, 10%, 15%, 25%, 30%, 40%, 50%, 60%, 80%, 85%, 90%, 95% 97%, 100%, or more relative to that of the unmodified parent moiety having Factor VIII activity, when measured in a suitable model, such as those well known in the art. Preferably, compounds having a hydrolytically stable linkage (e.g., an amide linkage) will possess at least some degree of the bioactivity of the unmodified parent moiety having Factor VIII activity.

Exemplary polymer conjugates in accordance with the invention will now be described wherein the moiety having Factor VIII activity is a protein. Typically, such a protein is expected to share (at least in part) a similar amino acid sequence as native Factor VIII. Thus, while reference will be made to specific locations or atoms within the native Factor VIII protein, such a reference is for convenience only and one having ordinary skill in the art will be able to readily determine the corresponding location or atom in other moieties having Factor VIII activity. In particular, the description provided herein for native Factor VIII is applicable to Factor VIIIa, Factor VIII:vWF, and B-domain deleted Factor VIII versions, as well as fragments, deletion variants, substitution variants or addition variants of any of the foregoing.

Amino groups on Factor VIII moieties provide a point of attachment between the Factor VIII moiety and the water-soluble polymer. Native Factor VIII comprises 158 amine-containing lysine residues (6.8 weight percent of the entire protein) and one amino terminus. With respect to Factor VIIIa, there are 78 lysine residues (5.5 weight percent of the entire protein) and two amino termini (resulting from the cleavage of Factor VIII). Consequently, notwithstanding secondary and tertiary structural considerations, both Factor VIII and Factor VIIIa (as well as any peptidic Factor VIII moiety, e.g., B-domain deleted Factor VIII) have several amines available for participation in conjugating reactions.

There are a number of examples of suitable water-soluble polymeric reagents useful for forming covalent linkages with available amines of a Factor VIII moiety. Specific examples, along with the corresponding conjugate, are provided in Table 1, below. In the table, the variable (n) represents the number of repeating monomeric units and "—NH—F8" represents the Factor VIII moiety following conjugation to the water-soluble polymer. While each polymeric portion presented in Table 1 terminates in a "$CH_3$" group, other groups (such as H and benzyl) can be substituted therefor.

TABLE 1

Amine-Specific Polymeric Reagents and the Factor VIII Moiety Conjugate Formed Therefrom Polymeric Reagent $H_3C-(OCH_2CH_2)_n-O-CH_2CH_2-C(=O)-O-N(\text{succinimidyl})$ mPEG-Succinimidyl Propionate $(\text{succinimidyl})N-O-C(=O)-CH_2CH_2-(OCH_2CH_2)_n-O-CH_2CH_2-C(=O)-O-N(\text{succinimidyl})$ Homobifunctional PEG-Succinimidyl Propionate $H_3C-(OCH_2CH_2)_n-O-CH_2CH_2CH_2-C(=O)-O-N(\text{succinimidyl})$ mPEG-Succinimidyl Butanoate $H_3C-(OCH_2CH_2)_n-O-C(=O)-O-\text{Benzotriazole}$ mPEG-Benzotriazole Carbonate $H_3C-(OCH_2CH_2)_n-NH-C(=O)-C_6H_4-O-C(=O)-O-N(\text{succinimidyl})$ mPEG-Succinimidyl Derivative Branched mPEG2-N-Hydroxysuccinimide:
$H_3C-(OCH_2CH_2)_n-O-C(=O)-NH-CH_2-CH_2-CH_2-CH_2-$
$H_3C-(OCH_2CH_2)_n-O-C(=O)-NH-$
joined at $CH-C(=O)-O-N(\text{succinimidyl})$ TABLE 1-continued
Amine-Specific Polymeric Reagents and the Factor VIII Moiety Conjugate Formed Therefrom
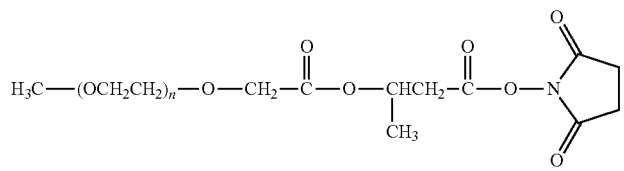
mPEG-Succinimidyl Derivative
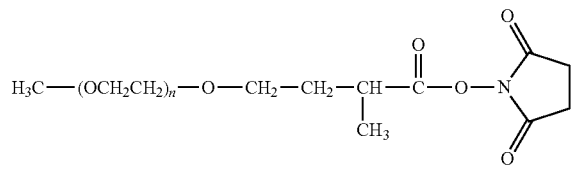
mPEG-Succinimidyl Derivative
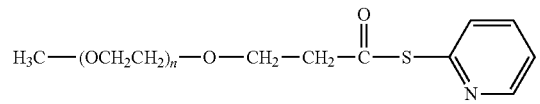
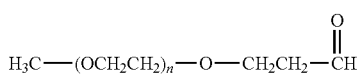
Homobifunctional PEG Propionaldehyde
mPEG Propionaldehyde
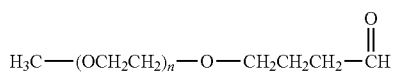
Homobifunctional PEG Butyraldehyde
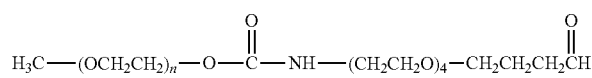
mPEG Butryaldehyde
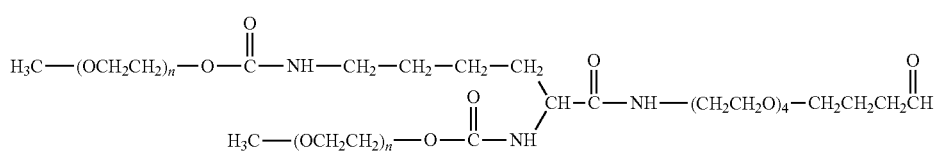
mPEG Butryaldehyde Derivative
Branched mPEG2 Butyraldehyde TABLE 1-continued Amine-Specific Polymeric Reagents and the Factor VIII Moiety Conjugate Formed Therefrom

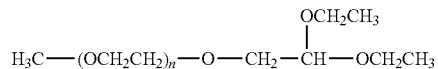

mPEG Acetal

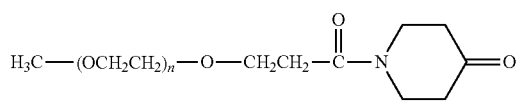

mPEG Piperidone

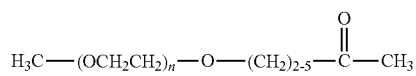

mPEG Methylketone

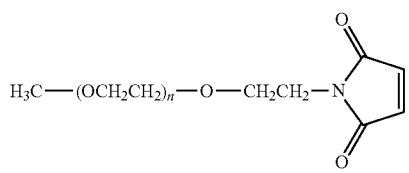

mPEG "Linkerless" Maleimide
(under certain reaction conditions such as pH > 8)

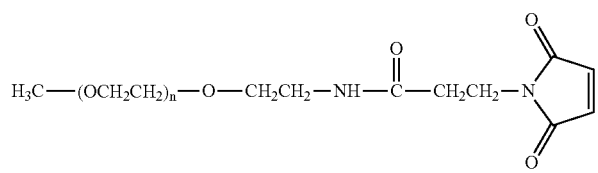

mPEG Maleimide Derivative
(under certain reaction conditions such as pH > 8)

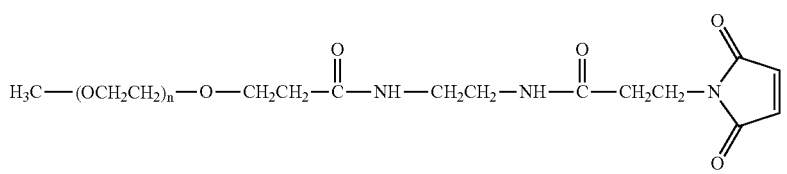

mPEG Maleimide Derivative
(under certain reaction conditions such as pH > 8)

TABLE 1-continued

Amine-Specific Polymeric Reagents and the Factor VIII Moiety Conjugate Formed Therefrom

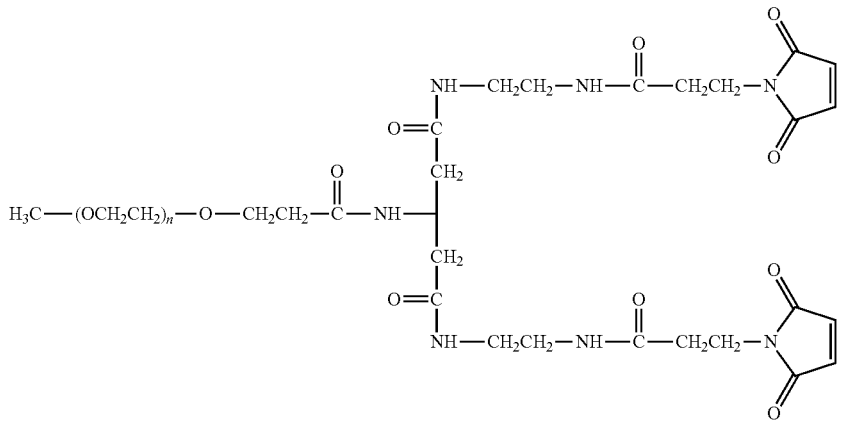

mPEG Forked Maleimide Derivative
(under certain reaction conditions such as pH > 8)

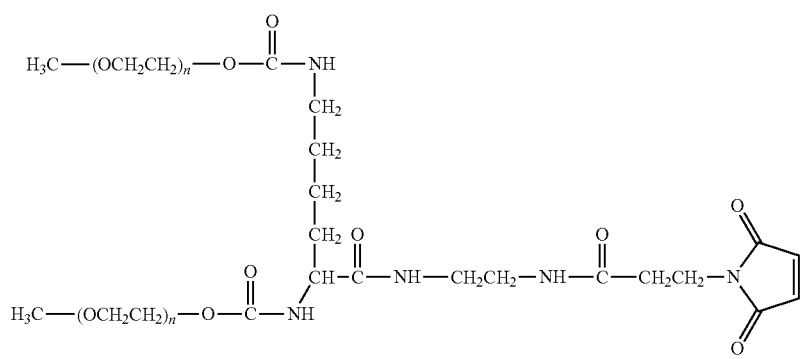

branched mPEG2 Maleimide Derivative
(under certain reaction conditions such as pH > 8)

Corresponding Conjugate

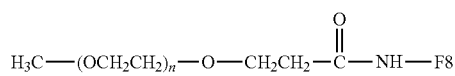

Amide Linkage

Amide Linkages

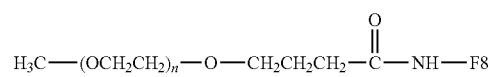

Amide Linkage

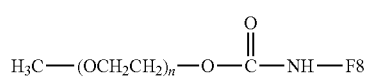

Carbamate Linkage

TABLE 1-continued

Amine-Specific Polymeric Reagents and the Factor VIII Moiety Conjugate Formed Therefrom

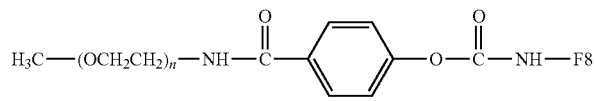

Carbamate Linkage

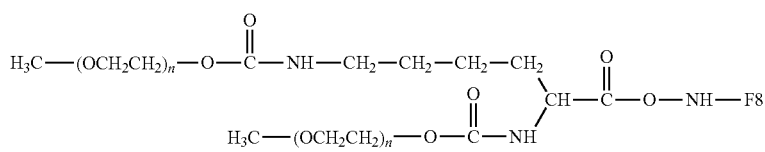

Amide Linkage

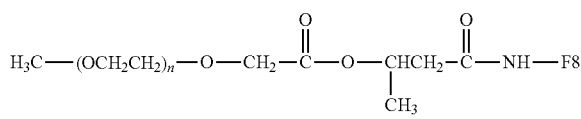

Amide Linkage

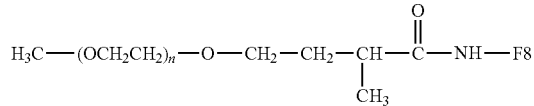

Amide Linkage

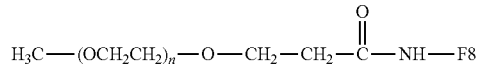

Amide Linkage

F8—NH—CH$_2$CH$_2$CH$_2$—(OCH$_2$CH$_2$)$_n$—O—CH$_2$CH$_2$—CH$_2$—NH—F8
Secondary Amine Linkages
H$_3$C—(OCH$_2$CH$_2$)$_n$—O—CH$_2$CH$_2$—CH$_2$—NH—F8
Secondary Amine Linkage
F8—NH—CH$_2$CH$_2$CH$_2$CH$_2$—(OCH$_2$CH$_2$)$_n$—O—CH$_2$CH$_2$CH$_2$—CH$_2$—NH—F8
Secondary Amine Linkage
H$_3$C—(OCH$_2$CH$_2$)$_n$—O—CH$_2$CH$_2$CH$_2$—CH$_2$—NH—F8
Secondary Amine Linkage

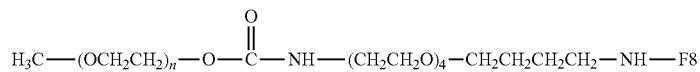

Secondary Amine Linkage

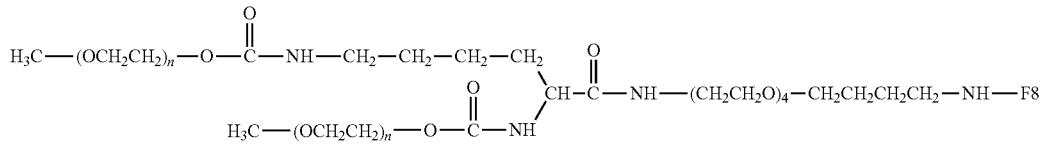

Secondary Amine Linkage

H$_3$C—(OCH$_2$CH$_2$)$_n$—O—CH$_2$CH$_2$—NH—F8
Secondary Amine Linkage

TABLE 1-continued
Amine-Specific Polymeric Reagents and the Factor VIII Moiety Conjugate Formed Therefrom
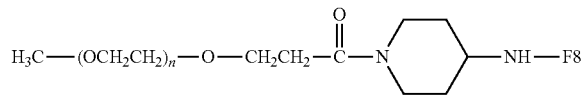
Secondary Amine Linkage
(to a secondary carbon)
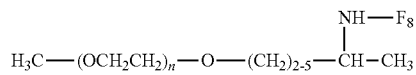
secondary amine linkage
(to a secondary carbon)
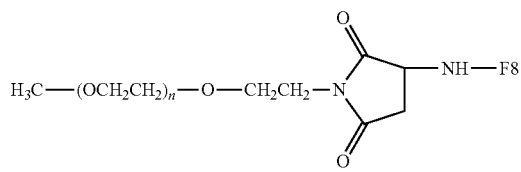
Secondary Amine Linkage
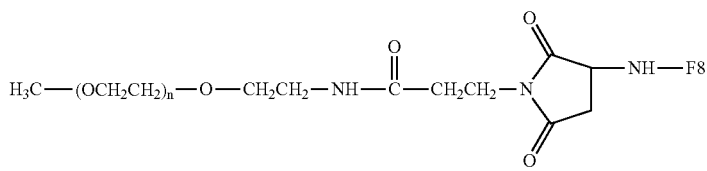
Secondary Amine Linkage
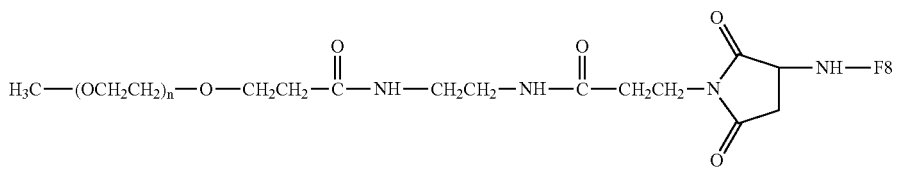
Secondary Amine Linkage
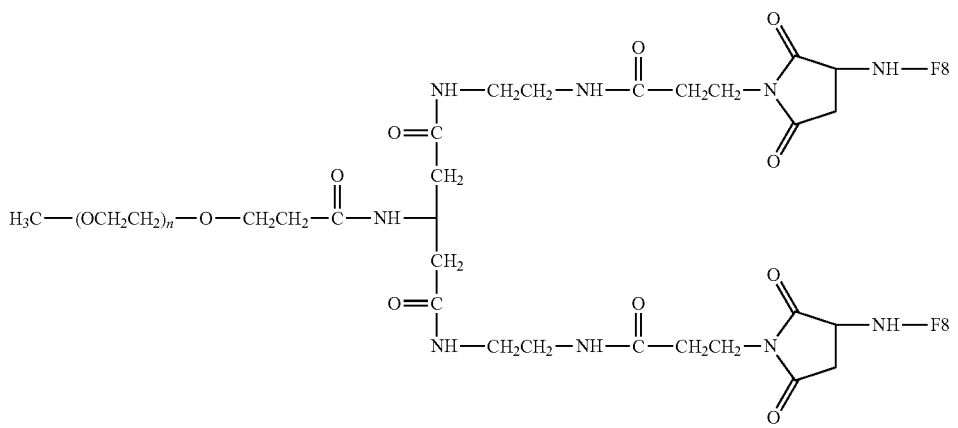
Secondary Amine Linkages

TABLE 1-continued

Amine-Specific Polymeric Reagents and the Factor VIII Moiety Conjugate Formed Therefrom

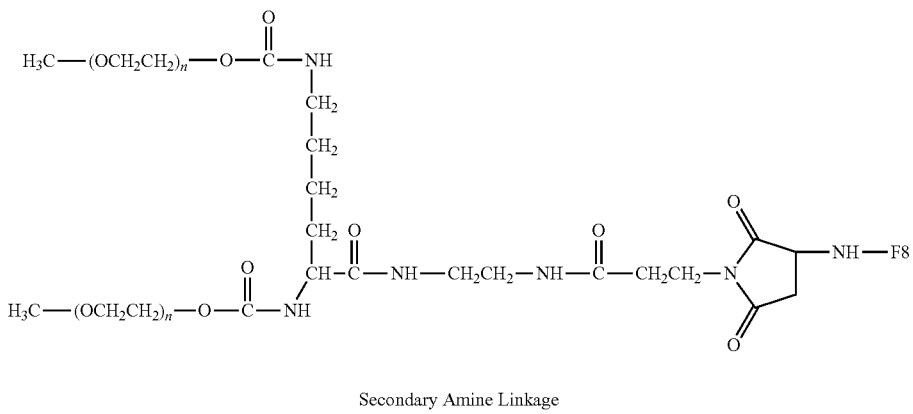

Secondary Amine Linkage

Conjugation of a polymeric reagent to an amino group of a Factor VIII moiety can be accomplished by one of ordinary skill in the art without undue experimentation. Typical of one approach is a reductive amination reaction used, for example, to conjugate a primary amine of a Factor VIII moiety with a polymer functionalized with a ketone, aldehyde or hydrated forms thereof (e.g., ketone hydrate, aldehyde hydrate). In this approach, the primary amine from the Factor VIII moiety reacts with the carbonyl group of the aldehyde or ketone (or the corresponding hydroxy-containing group of a hydrated aldehyde or ketone), thereby forming a Schiff base. The Schiff base, in turn, can then be reductively converted to a stable conjugate through use of a reducing agent such as sodium borohydride. Selective reactions (e.g., at the N-terminus are possible) are possible, particularly with a polymer functionalized with a ketone or an alpha-methyl branched aldehyde and/or under specific reaction conditions (e.g., reduced pH).

Preferred amine groups in Factor VIII that can serve as a site for attaching a polymer include those amine groups found within the following lysine residues: $Lys^{493}$, $Lys^{496}$, $Lys^{499}$, $Lys^{1804}$, $Lys^{1808}$, $Lys^{1813}$, $Lys^{1818}$, $Lys^{2183}$, $Lys^{2207}$, $Lys^{2227}$, $Lys^{2236}$, with $Lys^{496}$, $Lys^{1804}$, and $Lys^{1808}$ being particularly preferred. Numbering corresponds to the sequence provided in SEQ ID NO:2. As stated above, the amine group corresponding to each of these lysine residues in a protein other than human Factor VIII can serve as a useful site for conjugation. In addition, the N-terminus of any Factor VIII moiety that is a protein can serve as a polymeric attachment site.

Carboxyl groups represent another functional group that can serve as a point of attachment on the Factor VIII moiety. Structurally, the conjugate will comprise the following:

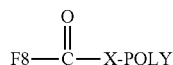

where F8 and the adjacent carbonyl group corresponds to the carboxyl-containing Factor VIII moiety, X is a linkage, preferably a heteroatom selected from O, N(H), and S, and POLY is a water-soluble polymer such as PEG, optionally terminating in an end-capping moiety.

The C(O)—X linkage results from the reaction between a polymeric derivative bearing a terminal functional group and a carboxyl-containing Factor VIII moiety. As discussed above, the specific linkage will depend on the type of functional group utilized. If the polymer is end-functionalized or "activated" with a hydroxyl group, the resulting linkage will be a carboxylic acid ester and X will be O. If the polymer backbone is functionalized with a thiol group, the resulting linkage will be a thioester and X will be S. When certain multi-arm, branched or forked polymers are employed, the C(O)X moiety, and in particular the X moiety, may be relatively more complex and may include a longer linkage structure.

Water-soluble derivatives containing a hydrazide moiety are also useful for conjugation at carboxyl groups. An example of such a derivative includes a polymer having the following structure:

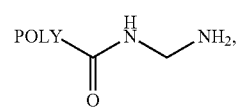

which, upon conjugation with a Factor VIII moiety, has the following structure:

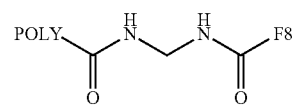

where F8 is the Factor VIII moiety following conjugation and POLY is a water-soluble polymer such as PEG, optionally terminating in an end-capping moiety.

Thiol groups contained within the Factor VIII moiety can serve as effective sites of attachment for the water-soluble polymer. In particular, cysteine residues provide thiol groups when the Factor VIII moiety is a protein. The thiol groups in such cysteine residues can then be reacted with an activated PEG that is specific for reaction with thiol groups, e.g., an N-maleimidyl polymer or other derivative, as described in U.S. Pat. No. 5,739,208 and in International Patent Publication No. WO 01/62827.

Specific examples, along with the corresponding conjugate, are provided in Table 2, below. In the table, the variable (n) represents the number of repeating monomeric units and "—S—F8" represents the Factor VIII moiety following conjugation to the water-soluble polymer. While each polymeric portion presented in Table 1 terminates in a "$CH_3$" group, other groups (such as H and benzyl) can be substituted therefor.

TABLE 2

Thiol-Specific Polymeric Reagents and the Factor VIII Moiety Conjugate Formed Therefrom Polymeric Reagent $H_3C-(OCH_2CH_2)_n-O-CH_2CH_2-\text{maleimide}$ mPEG "Linkerless" Maleimide $H_3C-(OCH_2CH_2)_n-O-CH_2CH_2-NH-C(=O)-CH_2CH_2-\text{maleimide}$ mPEG Maleimide Derivative $H_3C-(OCH_2CH_2)_n-O-CH_2CH_2-C(=O)-NH-CH_2CH_2-NH-C(=O)-CH_2CH_2-\text{maleimide}$ mPEG Maleimide Derivative mPEG Forked Maleimide Derivative structure:

$H_3C-(OCH_2CH_2)_n-O-CH_2CH_2-C(=O)-NH-CH[CH_2-C(=O)-NH-CH_2CH_2-NH-C(=O)-CH_2CH_2-\text{maleimide}]_2$ mPEG Forked Maleimide Derivative TABLE 2-continued
Thiol-Specific Polymeric Reagents and the Factor VIII Moiety Conjugate Formed Therefrom
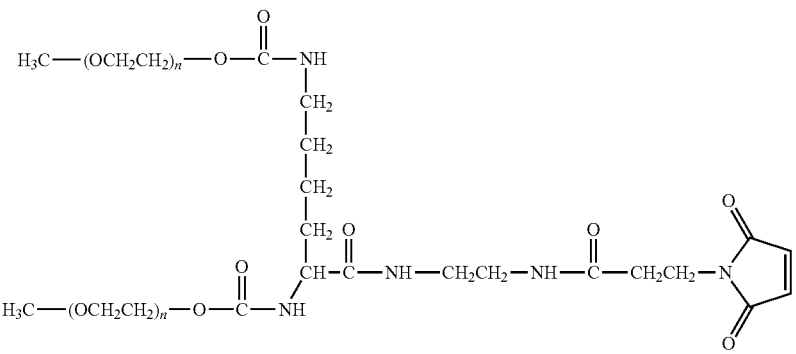
branched mPEG2 Maleimide Derivative
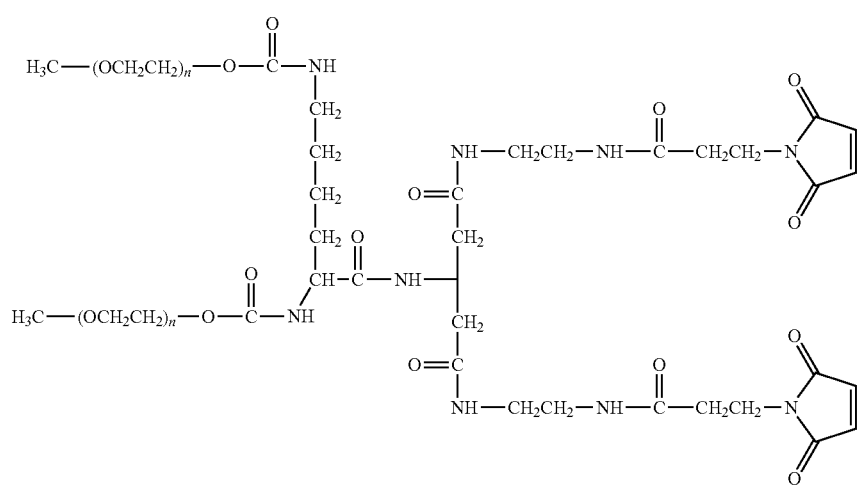
Branched mPEG2 Forked Maleimide Derivative
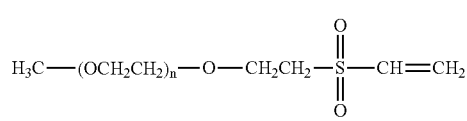
mPEG vinyl sulfone
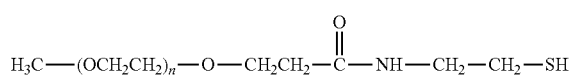
mPEG thiol
Corresponding Conjugate
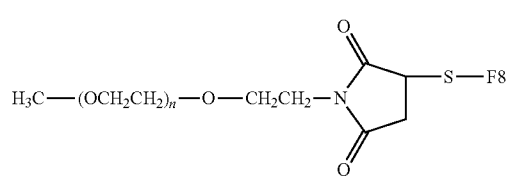
Thioether Linkage TABLE 2-continued
Thiol-Specific Polymeric Reagents and the Factor VIII Moiety Conjugate Formed Therefrom
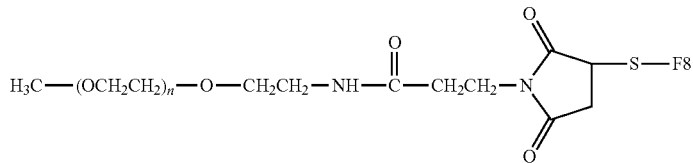
Thioether Linkage
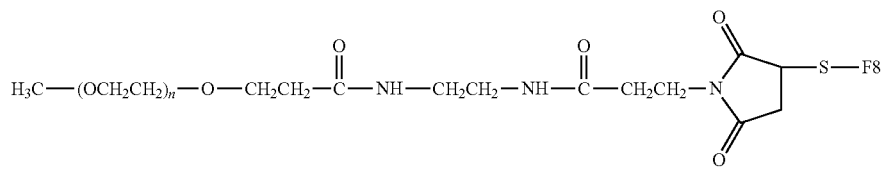
Thioether Linkage
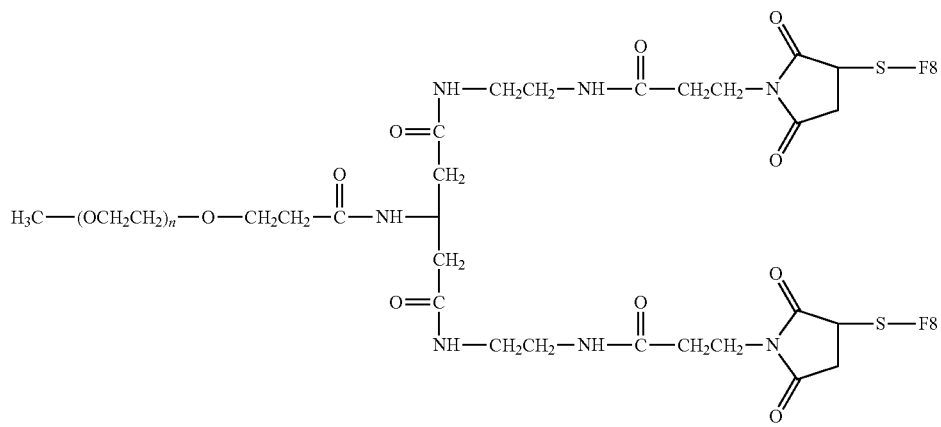
Thioether Linkage
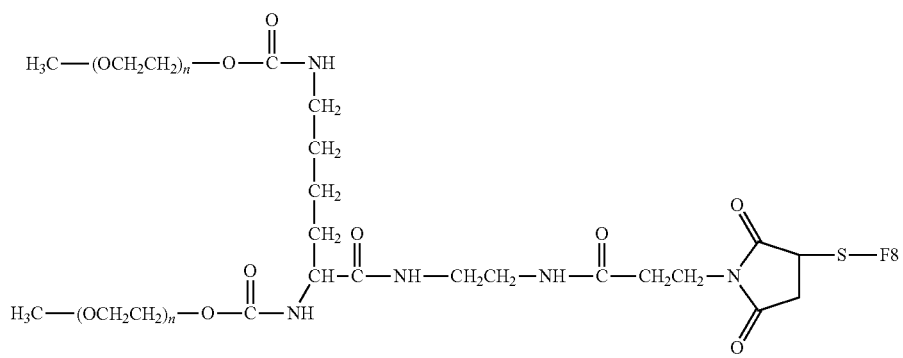
Thioether Linkage TABLE 2-continued Thiol-Specific Polymeric Reagents and the Factor VIII Moiety Conjugate Formed Therefrom

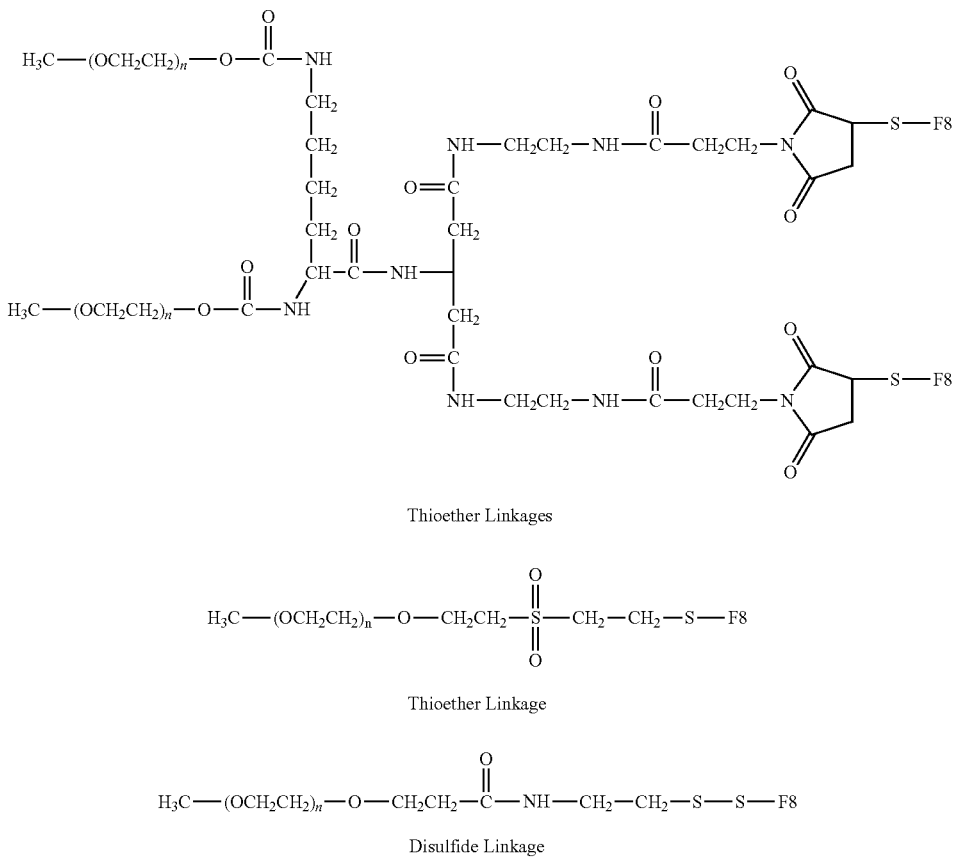

Thioether Linkages

Thioether Linkage

Disulfide Linkage

With respect to conjugates formed from water-soluble polymers bearing one or more maleimide functional groups (regardless of whether the maleimide reacts with an amine or thiol group on the Factor VIII moiety), the corresponding maleamic acid form(s) of the water-soluble polymer can also react with the Factor VIII moiety. Under certain conditions (e.g., a pH of about 7-9 and in the presence of water), the maleimide ring will "open" to form the corresponding maleamic acid. The maleamic acid, in turn, can react with an amine or thiol group of a Factor VIII moiety. Exemplary maleamic acid-based reactions are schematically shown below. POLY represents the water-soluble polymer, and F8 represents the Factor VIII moiety.

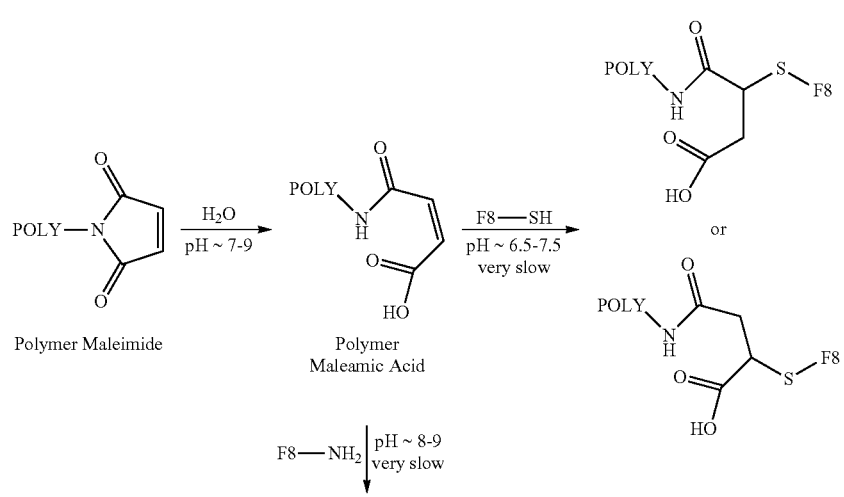

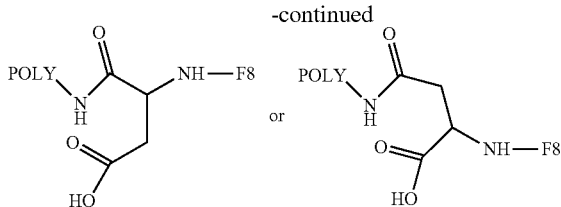

A representative conjugate in accordance with the invention can have the following structure:

POLY-L$_{0,1}$-C(O)Z—Y—S—S—F8 wherein POLY is a water-soluble polymer, L is an optional linker, Z is a heteroatom selected from the group consisting of O, NH, and S, and Y is selected from the group consisting of C$_{2-10}$ alkyl, C$_{2-10}$ substituted alkyl, aryl, and substituted aryl. Polymeric reagents that can be reacted with a Factor VIII moiety and result in this type of conjugate are described in copending application filed on Jan. 6, 2004, entitled "Thiol Selective Water Soluble Polymer Derivatives," and assigned U.S. Ser. No. 10/753,047.

Preferred thiol groups in Factor VIII that can serve as a site for attaching a polymeric reagent include those thiol groups found within the following Cysteine residues: Cys$^{248}$, Cys$^{310}$, Cys$^{329}$, Cys$^{630}$, Cys$^{692}$, Cys$^{711}$, Cys$^{1899}$, Cys$^{1903}$, and Cys$^{2000}$, with Cys$^{630}$, Cys$^{711}$, and Cys$^{1903}$, being particularly preferred. Numbering corresponds to the sequence provided in SEQ ID NO:2.

With respect to polymeric reagents, those described here and elsewhere can be purchased from commercial sources (e.g., Nektar Therapeutics, Huntsville Ala.). In addition, methods for preparing the polymeric reagents are described in the literature.

Typically, although not necessarily, the linkage between the Factor VIII moiety and the polymeric reagent includes one or more atoms such as one or more of carbon, nitrogen, sulfur, and combinations thereof. Preferably, the linkage comprises an amide, secondary amine, carbamate, thioether, or disulfide group. Optionally, additional atoms can connect the linkage to the chain of repeating monomers within the polymeric reagent. Nonlimiting examples of specific series of atoms connecting the Factor VIII moiety to the chain of repeating monomers include those selected from the group consisting of —O—, —S—, —S—S—, —C(O)—, —O—C(O)—, —C(O)—O—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—CH$_2$—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—C(O)—NH—CH$_2$—CH$_2$—NH—, —CH$_2$—CH$_2$—C(O)—NH—CH$_2$—CH$_2$—NH—C(O)—, —CH$_2$—CH$_2$—C(O)—NH—CH$_2$—CH$_2$—NH—C(O)—CH$_2$—, —CH$_2$—CH$_2$—C(O)—NH—CH$_2$—CH$_2$—NH—C(O)—CH$_2$—CH$_2$—, —O—C(O)—NH—[CH$_2$]$_{0-6}$—(OCH$_2$CH$_2$)$_{0-2}$—, —C(O)—NH—(CH$_2$)$_{1-6}$—NH—C(O)—, —NH—C(O)—NH—(CH$_2$)$_{1-6}$—NH—C(O)—, —O—C(O)—CH$_2$—, —O—C(O)—CH$_2$—CH$_2$—, and —O—C(O)—CH$_2$—CH$_2$—CH$_2$—.

The conjugates are typically part of a composition. Generally, the composition comprises a plurality of conjugates, preferably although not necessarily, each having one to three water-soluble polymers covalently attached to one Factor VIII moiety. The compositions, however, can also comprise other conjugates having four, five, six, seven, eight or more polymers attached to any given moiety having Factor VIII activity. In addition, the invention includes instances wherein the composition comprises a plurality of conjugates, each conjugate comprising one water-soluble polymer covalently attached to one Factor VIII moiety, as well as compositions comprising two, three, four, five, six, seven, eight, or more water-soluble polymers covalently attached to one Factor VIII moiety.

Control of the desired number of polymers for any given moiety can be achieved by selecting the proper polymeric reagent, the ratio of polymeric reagent to the Factor VIII moiety, temperature, pH conditions, and other aspects of the conjugation reaction. In addition, reduction or elimination of the undesired conjugates (e.g., those conjugates having four or more attached polymers) can be achieved through purification means.

For example, the polymer-Factor VIII moiety conjugates can be purified to obtain/isolate different conjugated species. Specifically, the product mixture can be purified to obtain an average of anywhere from one, two, three, four, five or more PEGs per Factor VIII moiety, typically one, two or three PEGs per Factor VIII moiety. The strategy for purification of the final conjugate reaction mixture will depend upon a number of factors, including, for example, the molecular weight of the polymeric reagent employed, the particular Factor VIII moiety, the desired dosing regimen, and the residual activity and in vivo properties of the individual conjugate(s).

If desired, conjugates having different molecular weights can be isolated using gel filtration chromatography and/or ion exchange chromatography. That is to say, gel filtration chromatography is used to fractionate differently numbered polymer-to-Factor VIII moiety ratios (e.g., 1-mer, 2-mer, 3-mer, and so forth, wherein "1-mer" indicates 1 polymer to Factor VIII moiety, "2-mer" indicates two polymers to Factor VIII moiety, and so on) on the basis of their differing molecular weights (where the difference corresponds essentially to the average molecular weight of the water-soluble polymer portion). For example, in an exemplary reaction where a 100,000 Dalton protein is randomly conjugated to a polymeric reagent having a molecular weight of about 20,000 Daltons, the resulting reaction mixture may contain unmodified protein (having a molecular weight of about 100,000 Daltons), monoPEGylated protein (having a molecular weight of about 120,000 Daltons), diPEGylated protein (having a molecular weight of about 140,000 Daltons), and so forth.

While this approach can be used to separate PEG and other polymer-Factor VIII moiety conjugates having different molecular weights, this approach is generally ineffective for separating positional isomers having different polymer attachment sites within the Factor VIII moiety. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) within Factor VIII moiety.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content (Sims et al. (1980) *Anal. Biochem*, 107: 60-63), and (iv) sodium dodecyl sulfate polyacrylamide gel electrophoresis (SDS PAGE), followed by staining with barium iodide.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

The compositions are preferably substantially free of proteins that do not have Factor VIII activity. In addition, the compositions preferably are substantially free of all other noncovalently attached water-soluble polymers. Moreover, at least one species of conjugate in the composition has at least one water-soluble water polymer attached to a moiety that transforms Factor X to Factor Xa. In some circumstances, however, the composition can contain a mixture of polymer-Factor VIII moiety conjugates and unconjugated Factor VIII.

Optionally, the composition of the invention further comprises a pharmaceutically acceptable excipient. If desired, the pharmaceutically acceptable excipient can be added to a conjugate to form a composition.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof An antioxidant can be present in the composition as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof A surfactant can be present as an excipient. Exemplary surfactants include: polysorbates, such as TWEEN 20™ (Polysorbate 20) and TWEEN® 80 (Polysorbate 80) and pluronics such as PLURONIC® F68 (polyoxyethylene-polyoxypropylene block copolymer) and PLURONIC® F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, furnaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate (i.e., the conjugate formed between the active agent and the polymeric reagent) in the composition will vary depending on a number of actors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D. C., 2000.

The compositions encompass all types of formulations and in particular those that are suited for injection, e.g., powders or lyophilates that can be reconstituted as well as liquids. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

The compositions of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical composition). As previously described, the conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The method of administering may be used to treat any condition that can be remedied or prevented by administration of the conjugate. Those of ordinary skill in the art appreciate which conditions a specific conjugate can effectively treat. For example, the conjugates can be used to treat individuals suffering from hemophilia A. In addition, the conjugates are suited for use as a prophylactic against uncontrolled bleeding, optionally in patients not suffering from hemophilia. Thus, for example, the conjugate can be administered to a patient at risk for uncontrolled bleeding prior to surgery.

The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering certain conjugates of the present invention is that individual water-soluble polymer portions can be cleaved off. Such a result is advantageous when clearance from the body is potentially a problem because of the polymer size. Optimally, cleavage of each water-soluble polymer portion is facilitated through the use of physiologically cleavable and/or enzymatically degradable linkages such as urethane, amide, carbonate or ester-containing linkages. In this way, clearance of the conjugate (via cleavage of individual water-soluble polymer portions) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer derivatives with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXPERIMENTAL

The practice of the invention will employ, unless otherwise indicated, conventional techniques of organic synthesis and the like, which are within the skill of the art. Such techniques are fully explained in the literature. See, for example, J. March, Advanced Organic Chemistry: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level.

Abbreviations

| | |
|---|---|
| DCM | dichloromethane |
| mPEG-SPA | mPEG-succinimidyl propionate |
| mPEG-SBA | mPEG-succinimidyl butanoate |
| mPEG-OPSS | mPEG-orthopyridyl-disulfide |
| mPEG-MAL | mPEG-maleimide, $CH_3O-(CH_2CH_2O)_n-CH_2CH_2-MAL$ |
| mPEG-SMB | mPEG-succinimidyl α-methylbutanoate, $CH_3O-(CH_2CH_2O)_n-CH_2CH_2-CH(CH_3)-C(O)-O$-succinimide |
| mPEG-ButyrALD | $CH_3O-(CH_2CH_2O)_n-CH_2CH_2-O-C(O)-NH-(CH_2CH_2O)_4CH_2CH_2CH_2C(O)H$ |
| mPEG-PIP | $CH_3O-(CH_2CH_2O)_n-CH_2CH_2-C(O)$-piperidin-4-one |
| SUC | succinimide or succinimidyl |
| NaCNBH$_3$ | sodium cyanoborohydride |
| HCl | hydrochloric acid |
| HEPES | 4-(2-hydroxyethyl)-1-piperazineethanesulfonic acid |
| NMR | nuclear magnetic resonance |
| DCC | 1,3-dicyclohexylcarbodiimide |
| DI | deionized |
| MW | molecular weight |
| r.t. | room temperature |
| K or kDa | kilodaltons |
| SEC | Size exclusion chromatography |
| HPLC | high performance liquid chromatography |
| FPLC | fast protein liquid chromatography |
| SDS-PAGE | sodium dodecyl sulfate-polyacrylamide gel electrophoresis |
| MALDI-TOF | Matrix Assisted Laser Desorption Ionization Time-of-Flight |

Materials:

All PEG reagents referred to in the appended examples are commercially available unless otherwise indicated.

mPEG-succinimidyl propionate, mPEG-SPA, molecular weight, 30K ($M_n$=31.3 kDa, Nektar Therapeutics)

mPEG-orthopyridyl-disulfide, mPEG-OPSS, molecular weight, 10K ($M_n$=10.3 kDa, Nektar Therapeutics)

mPEG-maleimide, mPEG-MAL, molecular weight, 20K (Mn=21.8 kDa, Nektar Therapeutics)

mPEG-maleimide, mPEG-MAL, molecular weight, 30K ($M_n$=31.4 kDa, Nektar Therapeutics)

mPEG-succinimidyl α-methylbutanoate, mPEG-SMB, molecular weight, 30K ($M_n$=30.5 kDa, Nektar Therapeutics)

mPEG-butyraldehyde, mPEG-ButyrALD, molecular weight, 30K ($M_n$=31.5 kDa, Nektar Therapeutics)

L-Histidine, biotechnology performance certified (Sigma)

HEPES, biotechnology performance certified, 99.5+% (Sigma)

Calcium chloride, dihydrate, for molecular biology, 99% (Sigma)

Sodium chloride, for molecular biology (Sigma)

TWEEN 80™ (Polyoxyethylene 20 sorbitan monooleate), Sigma Ultra, (Sigma)

Ethyl alcohol, USP, Absolute-200 Proof (AAPER)

Polyethylene glycol, MW 3,350, SigmaUltra (Sigma)

Slide-A-Lyzer Dialysis Cassette, 0.5-3 ml, or 3-12 ml capacity (Pierce)

Acetic acid, A.C.S. reagent, 99.7+% (Aldrich)

1N Acetic acid, volumetric standard (VWR)

1N Sodium hydroxide, volumetric standard (J. T. Baker)

Sodium cyanoborohydride, 95% (Aldrich)

Tris/glycine/SDS, 10×, protein electrophoresis buffer (Bio-Rad)

Laemmli sample buffer (Bio-Rad)

SigmaMarker, low range (M.W.6,500-66,000) (Sigma)

SigmaMarker, high range (M.W. 36,000-205,000) (Sigma)

7.5% Tris-HCl ready gel (10-well, 30 ul, Bio-Rad)

GelCode blue stain reagent (Pierce)

Methods (Analytical)

SEC-HPLC Analysis

Size exclusion chromatography (SEC) was performed on an Agilent 1100 HPLC system (Agilent). Samples were analyzed using a BIOSEP-SEC-S 4000 column (Phenomenex) and a mobile phase of 45 mM histidine, 4.5 mM calcium chloride, 0.36 M sodium chloride, 0.009% (v/v) TWEEN 80 (Polysorbate 80) and 10% ethyl alcohol, pH 6.7. The flow rate for the column was 0.3 ml/min. Eluted protein and PEG-protein conjugates were detected by UV at a wavelength of 280 nm.

SDS-PAGE Analysis

Samples were analyzed by sodium dodecyl sulfate-polyacrylamide gel electrophoresis (SDS-PAGE) using Mini-PROTEAN 3 Precast Gel Electrophoresis System (Bio-Rad). Samples were mixed with 2× Laemmli sample buffer, and were placed in a 95° C. water bath for ~5 minutes. Then, the prepared samples were loaded onto a 7.5% Tris-HCl ready gel and run for approximately 30 minutes at 200 V using Tris/glycine/SDS electrophoresis buffer.

Other Methods

Purification of PEG-Factor VIII Conjugates

A Superose 6 FIR 10/30, 24 ml gel filtration column (Amersham) was used with an FPLC system and AKTA prime system (Amersham) to purify the PEG-Factor VIII conjugates in Examples 6-11. The flow rate was 0.3 ml/min and the elution buffer was 50 mM Histidine, 0.5 M NaCl, 4.0 mM $CaCl_2$, and 0.01% (w/v) TWEEN 80™ (Polyoxyethylene 20 sorbitan monooleate), pH 6.7.

Buffer Exchange of Factor VIII Stock Solution

A Slide-A-Lyzer Dialysis Cassette (3-12 ml, 10,000 MWCO, Pierce) was removed from the protective pouch, and was soaked in MiliQ $H_2O$ for 15 minutes (water was changed every 5 minutes). The Factor VIII stock solution [0.398 mg/ml in 501 M Histidine, 0.5 M NaCl, 4.0 mM CaCl$_2$, 0.1% (w/v) PEG 3,350, 0.01% (w/v) TWEEN 80™ (Polyoxyethylene 20 sorbitan monooleate), pH 6.7] was then transferred into the cassette cavity through one of the guide ports on the top of the gasket. The cassette was placed in a 1 L beaker of HEPES buffer [50 mM HEPES, 0.5 M NaCl, 5 mM CaCl$_2$, 0.1% (w/v) PEG 3,350, 0.01% (v/v) TWEEN 80™ (Polyoxyethylene 20 sorbitan monooleate), pH 7.0] with a flotation buoy attached to the top of the cassette. The beaker was then placed on the stir plate to start the dialysis at 4° C. The HEPES buffer was changed for four times at intervals of 2-3 hrs, and was then left in a cold room (4° C.) for overnight dialysis. After dialysis, the cassette chamber was injected with air and the dialyzed sample was withdrawn from the cassette. The concentration of Factor VIII in HEPES buffer was measured at UV 280 nm from a SPECTRA max PLUS Spectrophotometer (Molecular Devices).

Example 1

PEGylation of B-Domain Deleted Factor VIII with mPEG-SPA, 20K mPEG-Succinimidyl propionate having a molecular weight of 20,000 Daltons is obtained from Nektar Therapeutics, (Huntsville, Ala.). The basic structure of the polymer reagent is provided below:

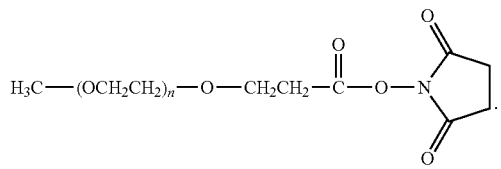

B-domain deleted Factor VIII is dissolved in deionized water, to which is added triethylamine to raise the pH to 7.2-9. To the above solution is added a 1.5 to 10-fold molar excess of the PEG reagent, mPEG-SPA. The resulting mixture is stirred at room temperature for several hours.

The reaction mixture is analyzed by SDS-PAGE to determine the degree of PEGylation of the protein. The degree of PEGylation, 1-mer, 2 mers, etc., can also be determined by any of a number of analytical techniques appropriate for proteins of this size, such as light angle scattering. The displayed peaks for native and mono-PEGylated species differ by approximately 20,000 Da. Increasing the ratio of PEG reagent to protein increases the degree of polyPEGylation, that is to say, the formation of 2-mers, 3-mers, etc.

Example 2

PEGylation of B-Domain Deleted Factor VIII with mPEG-SBA mPEG-Succinimidyl butanoate having a molecular weight of 10,000 daltons is obtained from Nektar Therapeutics, (Huntsville, Ala.). The basic structure of the polymer reagent is provided below:

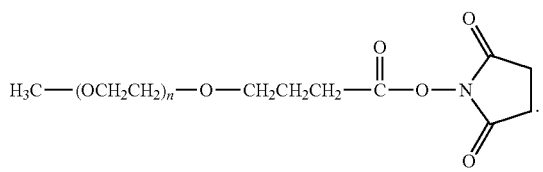

B-domain deleted Factor VIII is dissolved in deionized water, to which is added triethylamine to raise the pH to 7.2-9. To this solution is then added a 1.5 to 10-fold molar excess of mPEG-SBA. The resulting mixture is stirred at room temperature for several hours.

The reaction mixture is analyzed by SDS-PAGE to determine the degree of PEGylation of the protein.

Example 3

PEGylation of B-Domain Deleted Factor VIII with mPEG-MAL, 20K mPEG-Maleimide having a molecular weight of 20,000 daltons is obtained from Nektar Therapeutics, (Huntsville, Ala.). The basic structure of the polymer reagent is provided below:

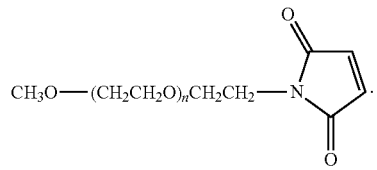

B-domain deleted Factor VIII is dissolved in buffer. To this protein solution is added a 3-5 fold molar excess of mPEG-MAL. The mixture is stirred at room temperature under an inert atmosphere for several hours. The reaction mixture is analyzed and purified by HPLC to provide a mixture of conjugated species.

Example 4

PEGylation of B-Domain Deleted Factor VIII with mPEG-OPSS, 20K

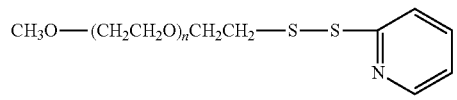

The sulfhydryl-selective polymer reagent, mPEG-orthopyridyl-disulfide (structure shown above), having a molecular weight of 20,000, is obtained from Nektar Therapeutics (Huntsville, Ala.). A five-fold molar excess of mPEG-OPSS is added to B-domain deleted Factor VIII in a buffered solution. The reaction mixture is stirred for several hours at room temperature under an inert atmosphere to form the desired conjugate having a disulfide linkage connecting the polymer to the protein.

Example 5

PEGylation of B-Domain Deleted Factor VIII with mPEG-PIP, 5K

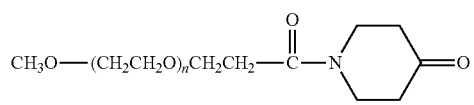

-continued

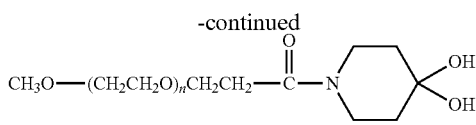

The above polymeric reagent, shown as both the ketone and corresponding ketal, is prepared as described in Nektar Therapeutics' Provisional Patent Application No. 60/437,325, entitled "Polymer Derivatives and Conjugates Thereof."

To prepare the above polymeric reagent, to a solution of methoxy-polyethylene glycol-succinimidyl propionate having a weight average molecular weight of 5,000 Daltons (1.0 g, 0.002 moles) in methylene chloride (20 ml), triethyl amine (0.084 ml, 0.006 moles) and 4-piperidone monohydrate hydrochloride (0.077 g, 0.005 moles) are added. The reaction mixture is stirred at room temperature under a nitrogen atmosphere overnight and then purified prior to conjugation. Alternatively, the polymer reagent may be purchased from Nektar Therapeutics.

To effect conjugation, to a solution of B-domain deleted Factor VIII in aqueous buffer is added a 20-fold molar excess of mPEG-PIP, 5K. The resulting solution is placed on a Roto Mix™ orbital shaker (Thermolyne Corp., Dubuque, Iowa) set at slow speed to facilitate reaction at room temperature. After 15 minutes, aqueous NaCNBH3 is added in an amount equal to a 50 fold-molar excess relative to the B-domain deleted Factor VIII. Aliquots are withdrawn at timed intervals from the reaction mixture and are analyzed by SDS-PAGE (using gels available from Bio-Rad Laboratories, Hercules, Calif.).

SDS-PAGE analysis indicates the presence of PEG derivatives of B-domain deleted Factor VIII having 1, 2, and 3 PEG moieties attached.

Example 6

Conjugation of B-Domain Deleted Factor VIII with mPEG-SPA, 30K

Prior to conjugation, a buffer exchange for B-domain deleted Factor VIII (Factor VIII) was performed to replace histidine with HEPES.

mPEG-SPA, 30K, stored at −20° C. under argon, was warmed to ambient temperature. The warmed mPEG-SPA (2.2 mg) was dissolved in 0.022 ml of 2 mM HCl to provide a 10% solution of polymer reagent. The mPEG-SPA solution was quickly added to 3 ml of Factor VIII solution [0.412 mg/ml in 50 mM HEPES, 0.5 M NaCl, 4.0 mM $CaCl_2$, 0.1% (w/v) PEG 3,350, 0.01% (w/v) TWEEN 80™ (Polyoxyethylene 20 sorbitan monooleate), pH 7.0] and mixed well. After 30 minutes of reaction at room temperature, the reaction vial was transferred to a cold room (4° C.), and another 0.022 ml of mPEG-SPA solution was added to the reaction mixture, and mixed well. The pH was determined (pH 7.0±0.2). The molar ratio of mPEG-SPA to protein was 20:1. The final mPEG-SPA concentration was 1.445 mg/ml, and the final Factor VIII concentration was 0.406 mg/ml. The reaction was allowed to proceed overnight at 4° C. on Rotomix (slow speed, Thermolyne). The resulting conjugate was assigned identifier "pz041701."

The conjugate mixture was purified using gel filtration chromatography. A size exclusion chromatography method was developed for analyzing the reaction mixtures, and the final products. SDS-PAGE analysis was also used for the characterization of the samples.

Figure 2:
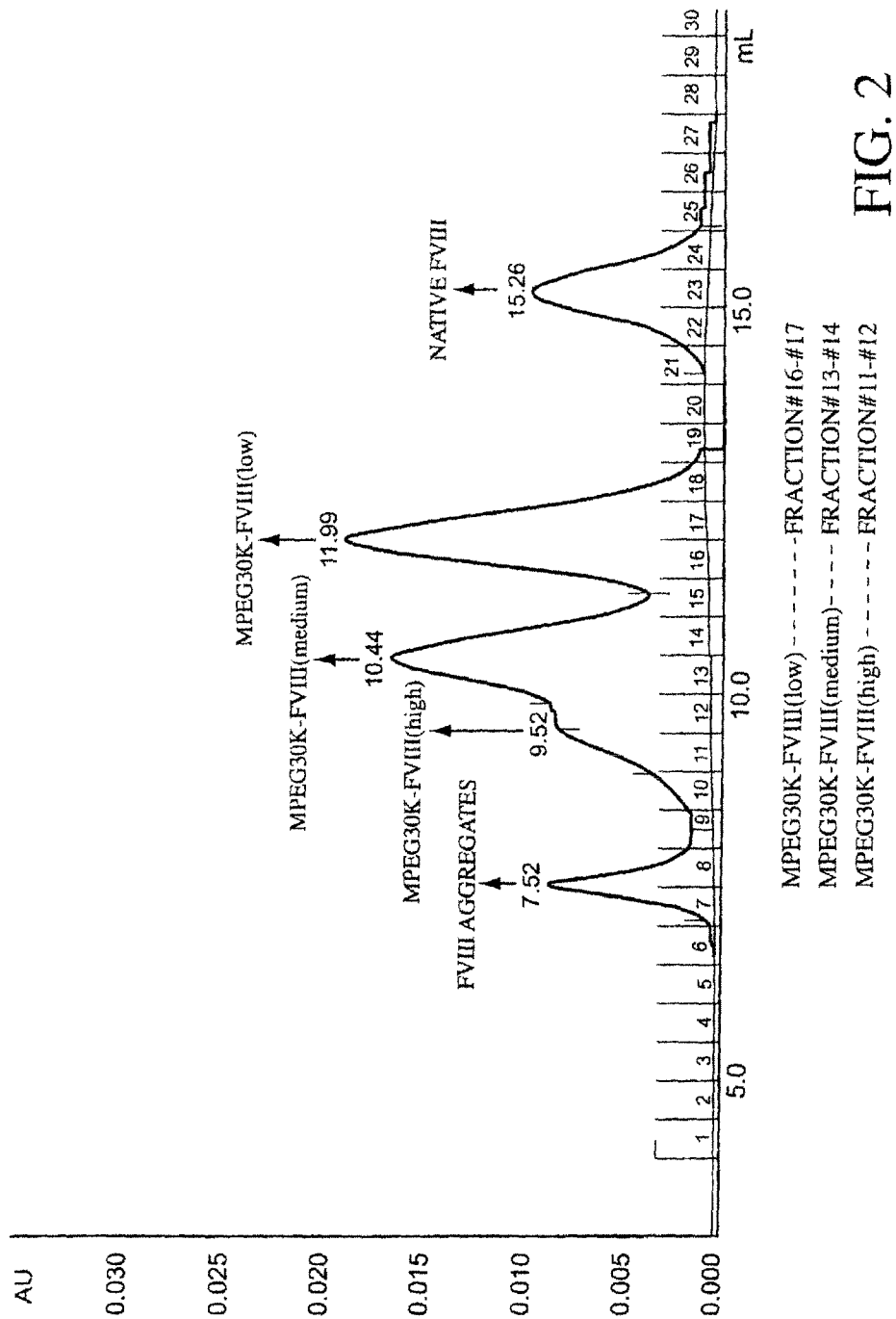
FIG. 2 is a SEC plot corresponding to purified B-Domain Deleted Factor VIII-PEG conjugate prepared by conjugating the protein to mPEG-SPA, 30K, as described in Example 6.

Conjugate Characterization. The resulting conjugate mixture, prior to purification, was a mixture of Factor VII PEG-monomer (or 1-mer), dimer (or 2-mer) and trimer (or 3-mer), corresponding to the identifiers "pz041701 (low)," "pz041701 (medium)," and "pz041701 (high)" respectively, as determined by SEC. That is to say: "pz041701 (low)" corresponds to mostly Factor VIII mono-PEGylated species or Factor VIII having one PEG moiety attached thereto; "pz041701 (medium)" corresponds to primarily Factor VIII di-PEGylated species, that is to say, Factor VIII having two PEG moieties attached thereto; and "pz041701 (high)" corresponds mostly to Factor VIII having three PEG moieties attached thereto. The corresponding SEC plots are shown in FIGS. 1 and 2. FIG. 1 shows the SEC plot corresponding to fractions collected upon SEC of the Factor VIII reaction mixture. According to the size exclusion chromatography (SEC) results, the PEGylation yield of mPEG-SPA-30K-FVIII (pz041701 low) was ~39%. The PEGylation yield of mPEG30-SPA-30K-FVIII (pz041701 medium) was ~32%, and the PEGylation yield of mPEG-SPA-30K-FVIII (pz041701 high) was ~11%, with percentages based upon relative amounts compared to all species present in the resulting reaction mixture. The conjugate mixture was further purified by FPLC and analyzed by SDS-PAGE.

Example 7

Conjugation of B-Domain Deleted Factor VIII with mPEG-MAL, 20K

Prior to the conjugation, a buffer exchange for B-domain deleted Factor VIII (Factor VIII) was performed to replace histidine with HEPES.

mPEG-MAL, 20K, stored at −20° C. under argon, was warmed to ambient temperature. The warmed mPEG-MAL reagent (4.4 mg) was dissolved in 0.044 ml of HEPES buffer [50 mM HEPES, 0.15 M NaCl, 4.0 mM $CaCl_2$, 0.01% (w/v) TWEEN 80™ (Polyoxyethylene 20 sorbitan monooleate), pH 7.0] to make a 10% mPEG-MAL solution. The mPEG-MAL solution was quickly added to 4 ml of Factor VIII solution [0.4324 mg/ml in 50 mM HEPES, 0.5 M NaCl, 4 mM $CaCl_2$, 0.1% (w/v) PEG 3,350, 0.01% (w/v) TWEEN 80™ (Polyoxyethylene 20 sorbitan monooleate), pH 7.0] and mixed well. After 30 minutes of reaction at room temperature, the reaction vial was transferred to the cold room (4° C.), and another 0.044 ml of mPEG-MAL solution was added to the reaction mixture, followed by the addition of three more aliquots of 0.044 ml of mPEG-MAL solution over the course of two hours. The pH was determined (pH 7.0±0.2). The molar ratio of mPEG-MAL to protein was 100:1. The final mPEG-MAL concentration was 5.213 mg/ml, and the final Factor VIII concentration was 0.410 mg/ml. The reaction was allowed to proceed overnight at 4° C. on Rotomix (slow speed, Thermolyne). The conjugate was assigned identifier "pz061201."

The conjugate mixture was purified using gel filtration chromatography. A size exclusion chromatography method was developed for analyzing the reaction mixtures, and the final products. SDS-PAGE analysis was also used for the characterization of the samples.

Figure 3:
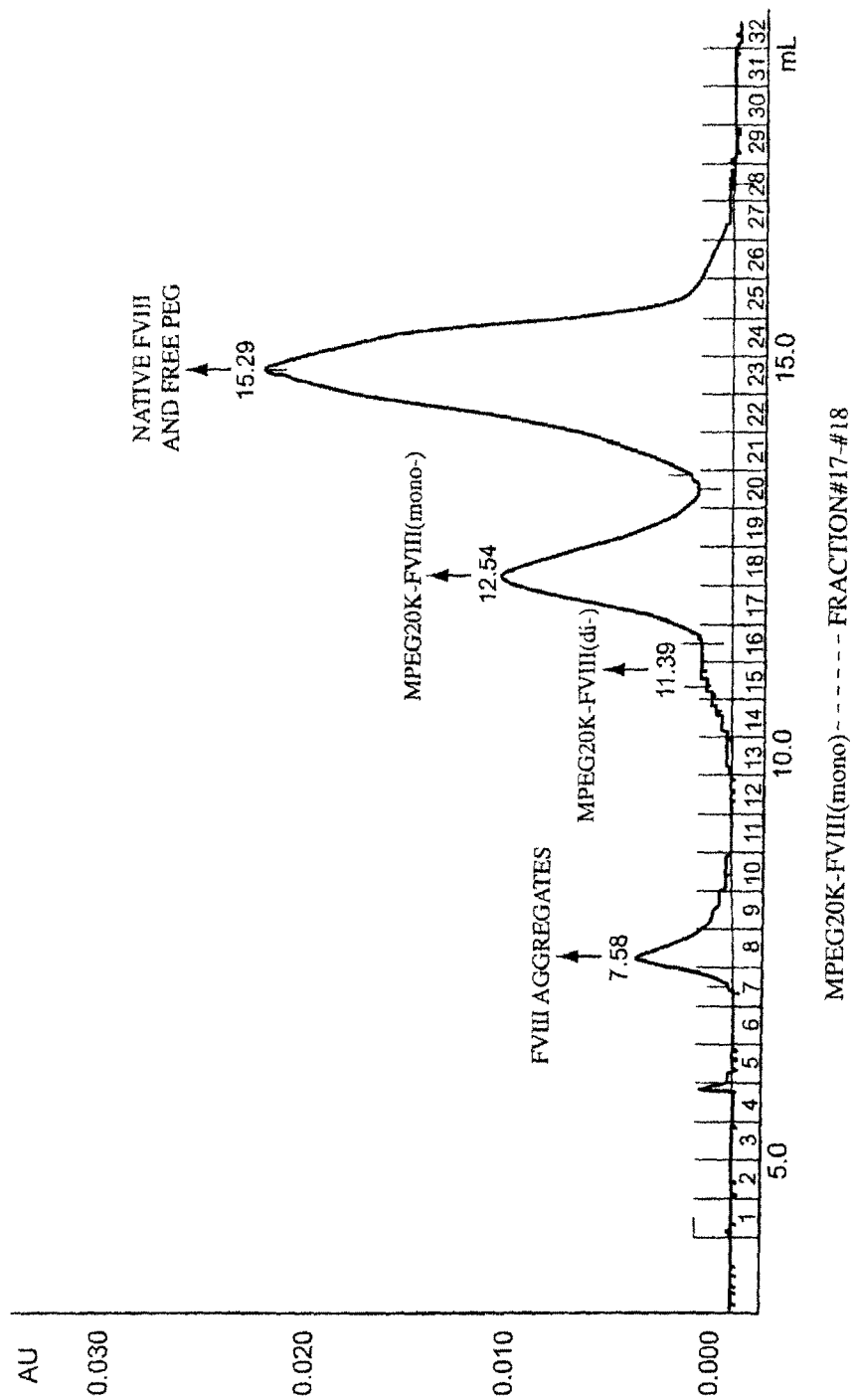
FIG. 3 is SEC plot corresponding to the reaction mixture formed upon PEGylation of B-Domain deleted Factor VIII with mPEG-MAL, 20K, as described in Example 7. As can be seen, the yield of monoPEGylated product was approximately 33%.
Figure 4:
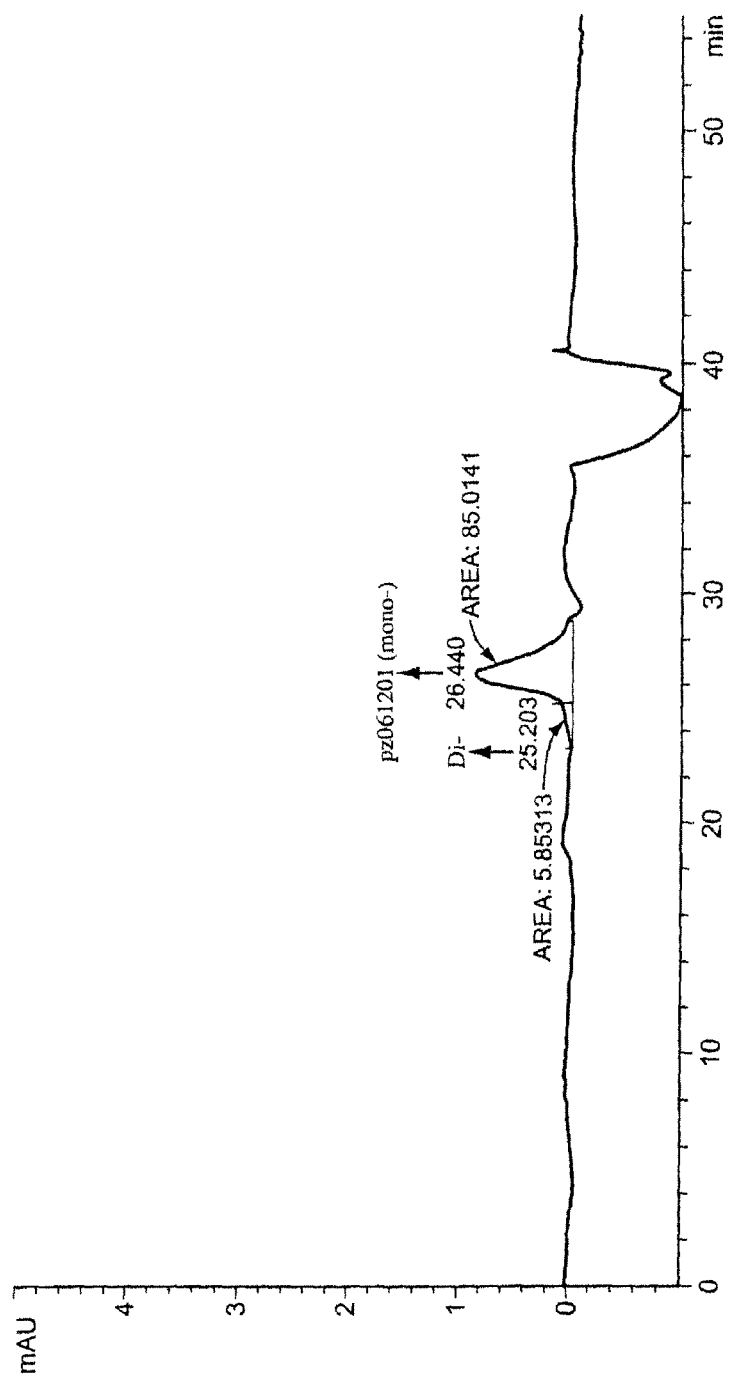
FIG. 4 is a SEC plot corresponding to purified B-Domain Deleted Factor VIII-PEG conjugate prepared by conjugating the protein to mPEG-MAL, 20K, as described in Example 7. The purified conjugate was ~94% PEG monomer.

CONJUGATE CHARACTERIZATION (Mono-PEGylated product). According to the size exclusion chromatography (SEC) results, the PEGylation yield of monoPEGylated conjugate (1-mer) was ~33% (FIG. 3). The Factor VIII conjugate mixture fractions were combined and purified by FPLC, and then further purified by gel filtration chromatography. The pz061201 final product was analyzed by both SDS-PAGE and SEC, and the purity of the "pz061201" product was determined to be approximately 94% Factor VIII PEG monomer (i.e., monopegylated Factor VIII), with ~6% Factor VIII PEG high-mers (FIG. 4).

Example 8

Conjugation of B-Domain Deleted Factor VIII with mPEG-SMB, 30K

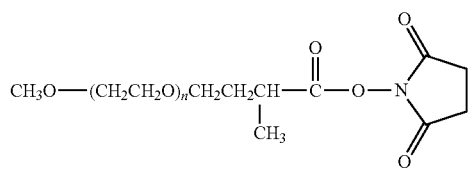

Prior to conjugation, a buffer exchange for B-domain deleted Factor VIII (Factor VIII) was performed to replace histidine with HEPES.

mPEG-SMB, 30K, stored at −20° C. under argon, was warmed to ambient temperature. The warmed mPEG-SMB (6.5 mg) was dissolved in 0.065 ml of 2 mM HCl to form a 10% mPEG-SMB solution. The mPEG-SMB solution was quickly added to 4 ml of Factor VIII solution [0.435 mg/ml in 50 mM HEPES, 0.5 M NaCl, 5.0 mM $CaCl_2$, 0.1% (w/v) PEG 3,350, 0.01% (v/v) TWEEN 80 (Polysorbate 80), pH 7.0] and mixed well. After 30 minutes of reaction at room temperature, the reaction vial was transferred to a cold room (4° C.). The pH was determined (pH 7.0±0.2). The molar ratio of mPEG-SMB to protein was 20:1. The final mPEG-SMB concentration was 1.599 mg/ml, and the final Factor VIII concentration was 0.428 mg/ml. The reaction was allowed to proceed for approximately 48 hrs at 4° C. on Rotomix (slow speed, Thermolyne), and was then quenched by the addition of acetic acid (99.7+%) to lower the pH to 6.0±0.3. The conjugate was assigned identifier "pz082501."

The conjugate mixture was purified using gel filtration chromatography. A size exclusion chromatography method was developed for analyzing the reaction mixtures, and the final products. SDS-PAGE analysis was also used for the characterization of the samples.

Figure 5:
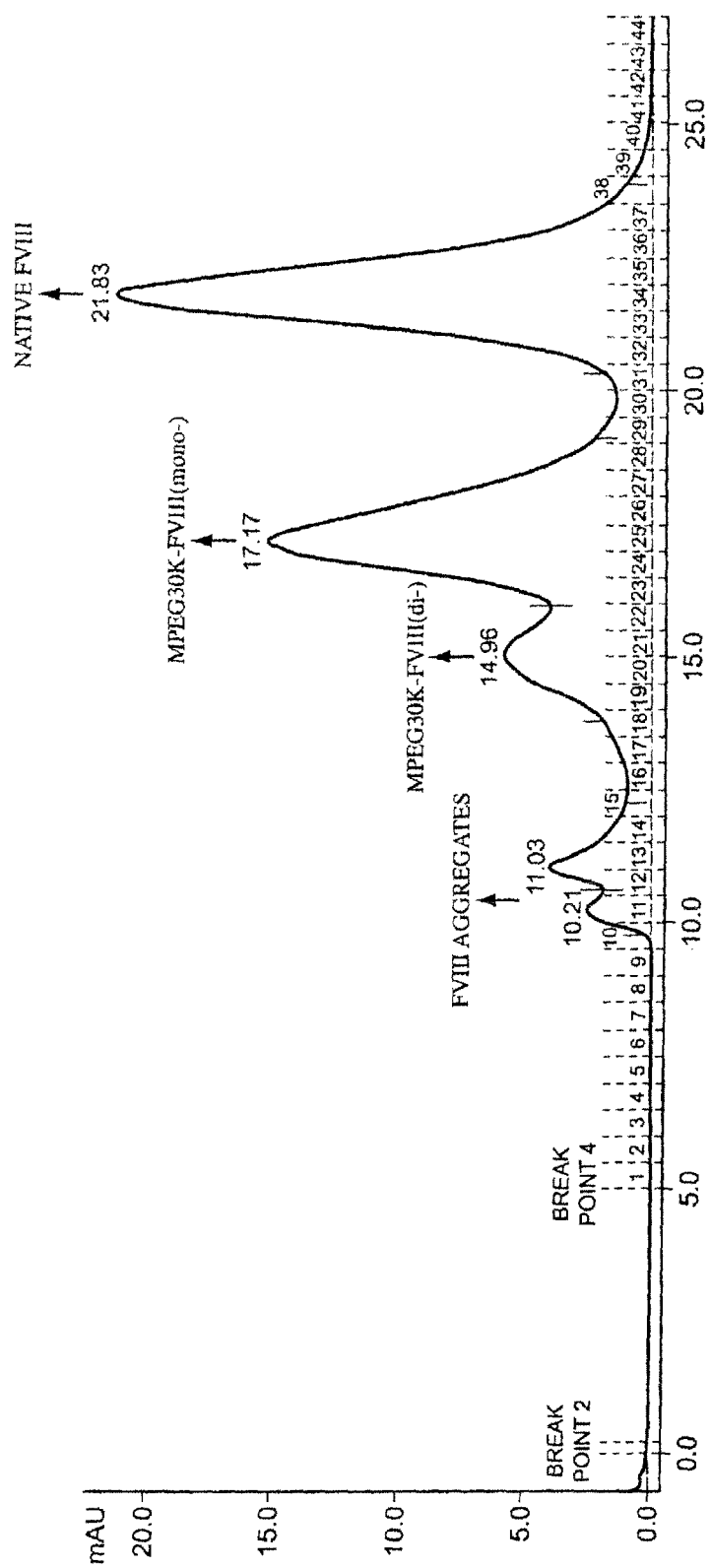
FIG. 5 is a SEC plot corresponding to the reaction mixture formed upon PEGylation of B-Domain Deleted Factor VIII with mPEG-SMB, 30K, as described in Example 8. The yield of monoPEGylated protein (1-mer) was approximately 41%.
Figure 6:
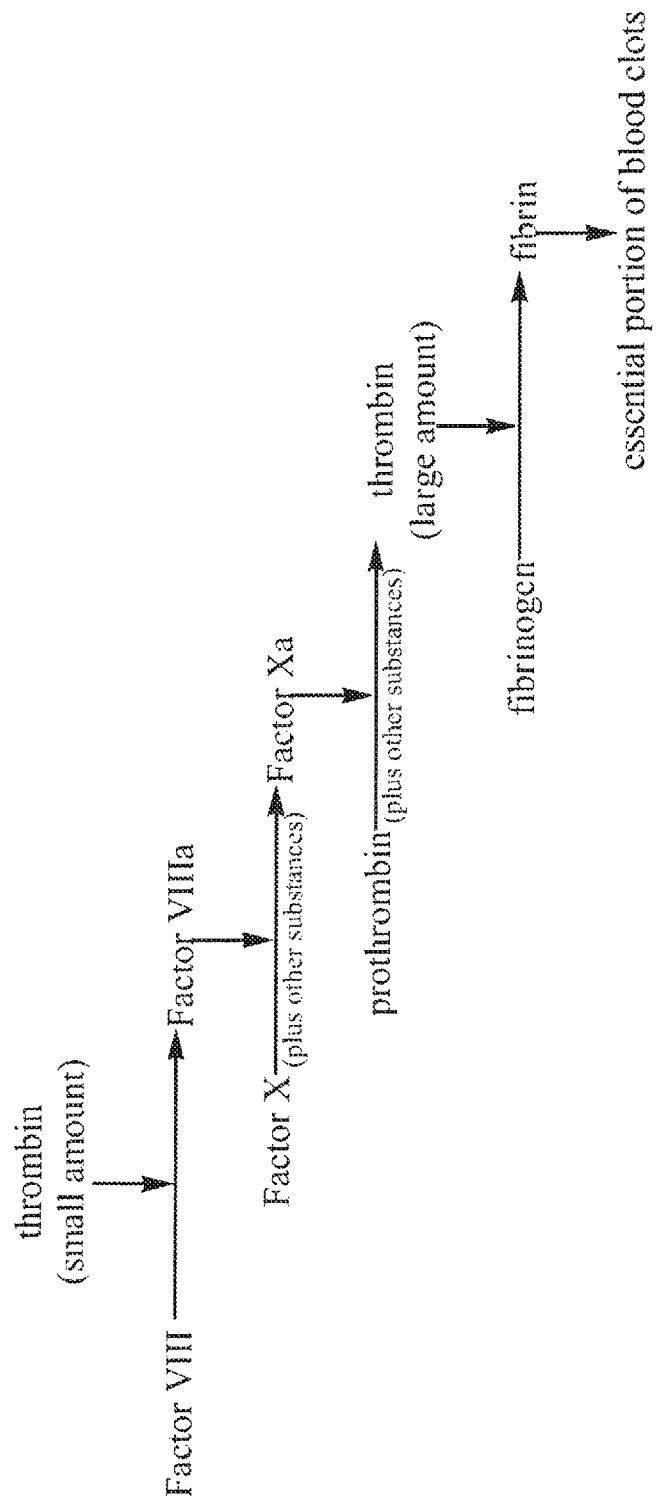
FIG. 6 demonstrates Factor VIII's role in the intrinsic pathway of blood clotting.

CONJUGATE CHARACTERIZATION: The mixture designated "pz082501" resulted from the PEGylation of Factor VIII with mPEG-SMB30K at pH 7.0±0.2. The conjugate mixture was purified and analyzed by SEC. Based upon the size exclusion chromatography (SEC) results, the PEGylation yield of pz082501, monoPEGylated conjugate (Factor VIII 1-mer) was ~41% (FIG. 5). The product mixture was further purified by FPLC and analyzed by SDS-PAGE and SEC. Characterization of the purified Factor VIII PEG conjugate product, pz082501, was ~95% mono-conjugated PEG Factor VIII with ~5% higher-mers.

Example 9

Conjugation of B-Domain Deleted Factor VIII with mPEG-OPSS, 10K

Prior to conjugation, a buffer exchange for B-domain deleted Factor VIII (Factor VIII) was performed to replace histidine with HEPES.

mPEG-OPSS, 10K, stored at −20° C. under argon, was warmed to ambient temperature. mPEG-OPSS (1.2 mg) was dissolved in 0.012 ml of $H_2O$ to make a 10% mPEG-OPSS solution. The mPEG-OPSS solution was quickly added to 0.5 ml of Factor VIII solution [0.398 mg/ml in 50 mM Histidine, 0.5 M NaCl, 4.0 mM $CaCl_2$, 0.1% (w/v) PEG 3,350, 0.01% (w/v) TWEEN 80™ (Polyoxyethylene 20 sorbitan monooleate), pH 6.7] and mixed well. After 30 minutes of reaction at room temperature, the reaction vial was transferred to a cold room (4° C.). The pH was determined (pH 6.7±0.2). The molar ratio of mPEG-OPSS-10K to protein was 100:1. The final mPEG-OPSS concentration was 2.344 mg/ml, and the final Factor VIII concentration was 0.389 mg/ml. The reaction was allowed to proceed overnight at 4° C. on Rotomix (slow speed, Thermolyne).

The conjugate mixture was purified using gel filtration chromatography. A size exclusion chromatography method was developed for analyzing the reaction mixtures, and the final products. SDS-PAGE analysis was also used for the characterization of the samples. The pegylation results and yields using the mPEG-OPSS reagent were similar to those in Example 7, which employed the mPEG-MAL reagent having a molecular weight of 20K.

Example 10

Conjugation of B-Domain Deleted Factor VIII with mPEG-MAL, 30K

Prior to conjugation, a buffer exchange for B-domain deleted Factor VIII (Factor VIII) was performed to replace histidine with HEPES.

mPEG-MAL, 30K, stored at −20K ° C. under argon, was warmed to ambient temperature. The warmed mPEG-MAL (1.0 mg) was dissolved in 0.010 ml of HEPES buffer [50 mM HEPES, 0.15 M NaCl, 4.0 mM $CaCl_2$, 0.01% (w/v) TWEEN 80™ (Polyoxyethylene 20 sorbitan monooleate), pH 7.0] to make a 10% mPEG-MAL solution. The mPEG-MAL solution was quickly added to 0.5 ml of Factor VIII solution [0.447 mg/ml in 50 mM HEPES, 0.5 M NaCl, 4 mM $CaCl_2$, 0.1% (w/v) PEG 3,350, 0.01% (w/v) TWEEN 80™ (Polyoxyethylene 20 sorbitan monooleate), pH 7.0] and mixed well. After 30 minutes of reaction at room temperature, the reaction vial was transferred to a cold room (4° C.), and another 0.010 ml of mPEG-MAL solution was added to the reaction mixture, followed by the addition of three more aliquots of 0.010 ml of mPEG-MAL solution over the course of two hours. The pH was determined (pH 7.0±0.2). The molar ratio of mPEG-MAL to protein was 100:1. The final mPEG-MAL concentration was 9.091 mg/ml, and the final Factor VIII concentration was 0.406 mg/ml. The reaction was allowed to proceed overnight at 4° C. on Rotomix (slow speed, Thermolyne).

The conjugate mixture was purified using gel filtration chromatography. A size exclusion chromatography method was developed for analyzing the reaction mixtures, and the final products. SDS-PAGE analysis was also used for the characterization of the samples. The PEGylation results and yields using the mPEG-MAL reagent having a molecular weight of 30 K were similar to those in Example 7, which employed the mPEG-MAL reagent having a molecular weight of 20K.

Example 11

Conjugation of B-Domain Deleted Factor VIII with mPEG-Butyr-ALD, 30K

Prior to conjugation, a buffer exchange for B-domain deleted Factor VIII (Factor VIII) was performed to replace histidine with HEPES.

mPEG-Butyr-ALD, 30K (shown above), stored at −20° C. under argon, was warmed to ambient temperature. The warmed mPEG-Butyr-ALD (3.8 mg) was dissolved in 0.038 ml of H$_2$O to make a 10% mPEG-Butyr-ALD solution. The mPEG-Butry-ALD solution was quickly added to 0.5 ml of Factor VIII solution [0.400 mg/ml in 50 mM HEPES, 0.5 M NaCl, 5 mM CaCl$_2$, 0.1% (w/v) PEG 3,350, 0.01% (v/v) TWEEN 80™ (Polyoxyethylene 20 sorbitan monooleate), pH 7.0] and mixed well. After 15 minutes, 0.060 ml of 10 mM sodium cyanoborohydride solution was added. The pH was determined (pH 7.0±0.2). The molar ratio of mPEG-Butyr-ALD to protein was 100:1. The final mPEG-Butyr-ALD concentration was 6.355 mg/ml. The final Factor VIII concentration was 0.334 mg/ml, and the final concentration of NaCNBH$_3$ was 1.003 mM. The reaction was allowed to proceed for 5 hours at room temperature, and then, overnight at 4° C. on Rotomix (slow speed, Thermolyne).

The conjugate mixture was purified using gel filtration chromatography. A size exclusion chromatography method was developed for analyzing the reaction mixtures, and the final products. SDS-PAGE analysis was also used for the characterization of the samples. The yield of Factor VIII mono-PEG conjugate was approximately 20%.

Example 12

In-Vitro Activity of Exemplary Factor VIII-PEG Conjugates

The in-vitro activities of the Factor VIII-PEG conjugates described in Examples 6, 7, and 8 were determined. All of the Factor VIII conjugates tested were bioactive.

---

What is claimed is:

1. A monoPEGylated Factor VIII conjugate comprising a single poly(ethylene glycol) polymer covalently attached to a cysteine residue of a B-domain deleted Factor VIII polypeptide, wherein the single poly(ethylene glycol) polymer is branched and has a nominal average molecular weight in a range of about 20,000 daltons to about 85,000 daltons.

2. The monoPEGylated Factor VIII conjugate of claim 1, wherein the single poly(ethylene glycol) polymer comprises PEG attached to a polyol core.

3. The monoPEGylated Factor VIII conjugate of claim 1, wherein the single poly(ethylene glycol) polymer has a nominal average molecular weight in a range of about 53,000 daltons to about 85,000 daltons.

4. The monoPEGylated Factor VIII conjugate of claim 1, wherein the single poly(ethylene glycol) polymer has a nominal average molecular weight selected from the group consisting of about 20,000 Daltons, about 22,500 Daltons, about 25,000 Daltons, about 30,000 Daltons, about 40,000 Daltons, about 50,000 Daltons, about 60,000 Daltons, and about 75,000 Daltons.

5. The monoPEGylated Factor VIII conjugate of claim 1, wherein the cysteine residue to which the single poly(ethylene glycol) polymer is covalently attached is one that has been added to or substituted in the B-domain deleted Factor VIII polypeptide.

6. The monoPEGylated Factor VIII conjugate of claim 3, wherein the cysteine residue to which the single poly(ethylene glycol) polymer is covalently attached is one that has been added to or substituted in the B-domain deleted Factor VIII polypeptide.

7. The monoPEGylated Factor VIII conjugate of claim 6, wherein the added or substituted cysteine residue to which the single poly(ethylene glycol) polymer is covalently attached is located within the A1 subunit of the B-domain deleted Factor VIII polypeptide.

8. The monoPEGylated Factor VIII conjugate of claim 6, wherein the added or substituted cysteine residue to which the single poly(ethylene glycol) polymer is covalently attached is located within the A2 subunit of the B-domain deleted Factor VIII polypeptide.

9. The monoPEGylated Factor VIII conjugate of claim 6, wherein the added or substituted cysteine residue to which the single poly(ethylene glycol) polymer is covalently attached is located within the A3 subunit of the B-domain deleted Factor VIII polypeptide.

10. The monoPEGylated Factor VIII conjugate of claim 6, wherein the added or substituted cysteine residue to which the single poly(ethylene glycol) polymer is covalently attached is located within the C1 subunit of the B-domain deleted Factor VIII polypeptide.

11. The monoPEGylated Factor VIII conjugate of claim 6, wherein the added or substituted cysteine residue to which the single poly(ethylene glycol) polymer is covalently attached is located within the C2 subunit of the B-domain deleted Factor VIII polypeptide.

12. The monoPEGylated Factor VIII conjugate of claim 6, wherein a thiol group of the cysteine residue is covalently attached to the single poly(ethylene glycol) polymer via reaction with an N-maleimidyl group of the poly(ethylene glycol) polymer.

13. The monoPEGylated Factor VIII conjugate of claim 12, wherein the linkage between the single poly(ethylene glycol) polymer and the B-domain deleted Factor VIII polypeptide comprises, in addition to a thioether bond, a residue of an N-maleimidyl group to which the thioether sulfur is covalently attached.

14. The monoPEGylated Factor VIII conjugate of claim 13, wherein the single poly(ethylene glycol) polymer comprises a series of atoms connecting the cysteine residue of the B-domain deleted Factor VIII polypeptide to a chain of repeating monomers within the single poly(ethylene glycol) polymer.

15. The monoPEGylated Factor VIII conjugate of claim 14, wherein the series of atoms connecting the cysteine residue of the B-domain deleted Factor VIII polypeptide to the chain of repeating monomers within the single poly(ethylene glycol) polymer includes an amide group.

16. The monoPEGYlated Factor VIII conjugate of claim 14, wherein the single poly(ethylene glycol) polymer comprises terminal methoxy capping groups.

17. The monoPEGylated Factor VIII conjugate of claim 16, wherein the conjugate is bioactive.

18. The monoPEGylated Factor VIII conjugate of claim 1, wherein the single poly(ethylene glycol) polymer is covalently attached to the cysteine residue of the B-domain deleted Factor VIII polypeptide via a thioether bond.

19. The monoPEGylated Factor VIII conjugate of claim 1, wherein the single poly(ethylene glycol) polymer has a nominal average molecular weight of about 60,000 daltons.

20. The monoPEGylated Factor VIII conjugate of claim 3, wherein the cysteine residue to which the single poly(ethylene glycol) polymer is covalently attached is located within the A3 subunit of the B-domain deleted Factor VIII polypeptide.

21. The monoPEGylated Factor VIII conjugate of claim 20, wherein the single poly(ethylene glycol) polymer has a nominal average molecular weight of about 60,000 daltons.

22. The monoPEGylated Factor VIII conjugate of claim 21, wherein the cysteine residue to which the single poly(ethylene glycol) polymer is covalently attached is one that has been added to or substituted in the B-domain deleted Factor VIII polypeptide.

* * * * *